United States Patent [19]
King et al.

[11] Patent Number: 5,864,019
[45] Date of Patent: Jan. 26, 1999

[54] MULTIVALENT ANTIGEN-BINDING PROTEINS

[75] Inventors: David John King, Surrey; Andrew Mountain, Berkshire; Raymond John Owens, Oxfordshire; Geoffrey Thomas Yarranton, Berkshire, all of United Kingdom

[73] Assignee: Celltech Limited, Berkshire, United Kingdom

[21] Appl. No.: 400,115

[22] Filed: Mar. 6, 1995

Related U.S. Application Data

[63] Continuation of Ser. No. 127,136, Sep. 27, 1993, abandoned, which is a continuation of Ser. No. 842,193, filed as PCT/GB91/00935 Jun. 11, 1991, abandoned.

[30] Foreign Application Priority Data

Jun. 11, 1990 [GB] United Kingdom ............... 9012995.8

[51] Int. Cl.$^6$ .................................................. A61K 39/395
[52] U.S. Cl. ...................................... 530/367.3; 424/133.1; 424/134.1; 424/135.1; 424/136.1; 530/391.1
[58] Field of Search .......................... 530/387.3, 391.1; 435/69.6; 424/133.1, 136.1, 135.1, 134.1

[56] References Cited

U.S. PATENT DOCUMENTS 4,474,893 10/1984 Reading .................................. 436/547
4,722,899 2/1988 Hamaoka et al. ................... 435/172.2

FOREIGN PATENT DOCUMENTS 8809344 12/1988 WIPO.

OTHER PUBLICATIONS

Harris et al. TibTech vol. 11,42 1993.
Waldmann Science vol. 252 1657, 1991.
Hird et al. Genes and Cancer 184 1992, John Wiley and Sons.
Journal of Molecular Biology, Angos. 211. Feb. 20, 1990. p. 943.

Seaver Genetic Engineering News vol 14 No. 14 pp. 10 and 21, 1994.

Sevier et al. Clin Chem vol. 27 No. 11 1797–1806, 1981.

Chester et al. TIBTECH vol. 13 294–300, 1995.

Gottstein et al. Annals of Oncology vol. 5 Supl 1 S97–S103, 1994.

Jain Scientific American vol. 271 (1) 58, Jul. 1994.

*Primary Examiner*—Sheela Huff
*Assistant Examiner*—Julie E. Reeves
*Attorney, Agent, or Firm*—Foley & Lardner

[57] ABSTRACT

A multivalent antigen-binding protein comprises a first Fv fragment bound to at least one further Fv fragment by a connecting structure which links the Fv fragments to each other but which maintains them spaced apart such that the proteins are capable of binding to adjacent antigenic determinants. Typically the connecting structure comprises a spacing polypeptide sequence, which may be about 3 to 16 amino acids in length, connected to a linkage unit which may be a synthetic chemical linker, e.g., a maleimide linker, or is a polypeptide sequence leading from the spacing sequence. In a particularly preferred embodiment, the multivalent antigen binding protein comprises a VH domain having attached to its C-terminal end a V-C joining sequence and an antibody hinge sequence. Preferably one or more of the Fv fragments is a single chain Fv (scFv). The proteins are preferably prepared by recombinant DNA techniques and are useful for in vivo therapeutic and especially diagnostic applications.

21 Claims, 15 Drawing Sheets

FIG. 1(A)

```
1   CCACTGACTCTAAACCATGGAATGGAGCTGGGTCTTTCTCTTCCTGTCAGTAACTACA   60
    ----------+---------+---------+---------+---------+---------+
    GGTGACTGAGATTGGTACCTTACCTCGACCCAGAAAGAGAAGGACAGTCATTGATGT

M  E  W  S  W  V  F  L  F  F  L  S  V  T  T

61  GGTGTCCACTCCCAGGTTCAGCTGCAGCAGTCTGACGCTGAGTTGGTGAAACCTGGGGCT  120
    ----------+---------+---------+---------+---------+---------+
    CCACAGGTGAGGGTCCAAGTCGACGTCGTCAGACTGCGACTCAACCACTTTGGACCCCGA

G  V  H  S  Q  V  Q  L  Q  Q  S  D  A  E  L  V  K  P  G  A

121 TCAGTGAAGATATCCTGCAAGGCTTCTGGCTACACCTTCACTGACCATGCTATTCACTGG  180
    ----------+---------+---------+---------+---------+---------+
    AGTCACTTCTATAGeGACGTTCCGAAGACCGATGTGGAAGTGACTGGTACGATAAGTGACC

S  V  K  I  S  C  K  A  S  G  Y  T  F  T  D  H  A  I  H  W

181 GCGAAGCAGAAGCCTGAACAGGCCTGGAATGGATTGGATATATTTCTCCCGGAAATGAT  240
    ----------+---------+---------+---------+---------+---------+
    CGCTTCGTCTTCGGACTTGTCCGGACCTTACCTAACCTATATAAAGAGGGCCTTTACTA

```
     GATATTAAGTACAATGAGAAGTTCAAGGGCCAAGGCCACACTGACTGCAGACAAATCCTCC
241  ------------+---------+---------+---------+---------+---------  300
     CTATAATTCATGTTACTCTTCAAGTTCCCGTTCCGGTGTGACTGACGTCTGTTTAGGAGG

D  I  K  Y  N  E  K  F  K  G  K  A  T  L  T  A  D  K  S  S

AGCACTGCCTACATGCAGCTCAACAGCCTGACATCTGAGGATTCTGCAGTGTATTTCTGT
301  ------------+---------+---------+---------+---------+---------  360
     TCGTGACGGATGTACGTCGAGTTGTCGGACTGTAGACTCCTAAGACGTCACAGAAAGACA

S  T  A  Y  M  Q  L  N  S  L  T  S  E  D  S  A  V  Y  F  C

AAAAGATCGTACTACGGCCACTGGGGCCAAGGCACCACTCTCACAGTCTCCTCAGCTTCC
361  ------------+---------+---------+---------+---------+---------  420
     TTTTCTAGCATGATGCCGGTGACCCCGGTTCCGTGGTGAGAGTGTCAGAGGAGTCGAAGG

K  R  S  Y  Y  G  H  W  G  Q  G  T  T  L  T  V  S  S  A  S

ACCAAGGGCGAGTCCAAATATGGTCCCCCATGCCCCATCAGCCCCATGATGAATT
421  ------------+---------+---------+---------+---------+------      474
     TGGTTCCCGCTCAGGTTTATACCAGGGGTACGGGTAGTCGGGTACTACTTAA

```
    AAAATGAAAAAGACAGCTATCGCGATTGCAGTGGCACTGGCTGGTTTCGCTACCGTAGCG
1   ---------+---------+---------+---------+---------+---------+
      K  M  K  K  T  A  I  A  I  A  V  A  L  A  G  F  A  T  V  A

CAAGCTGATATCCAGATGACTCAGTCTCCAGCCTCCCTATCTGTATCTGTGGGAGAAACT
61  ---------+---------+---------+---------+---------+---------+
      Q  A  D  I  Q  M  T  Q  S  P  A  S  L  S  V  S  V  G  E  T

GTCACCATCACATGTCGAGCAAGTGAGAATATTTACAGTAATTTAGCATGGTATCAACAG
121 ---------+---------+---------+---------+---------+---------+
      V  T  I  T  C  R  A  S  E  N  I  Y  S  N  L  A  W  Y  Q  Q

AAACAGGGAAAATCTCCTCAGCTCCTGGTCTATGCTGCAACAAACTTAGCAGATGGTGTG
181 ---------+---------+---------+---------+---------+---------+
      K  Q  G  K  S  P  Q  L  L  V  Y  A  A  T  N  L  A  D  G  V

CCATCAAGGTTCAGTGGCAGTGGATCGGGCACACAGTATTCCCTCAAGATCAACAGCCTG
241 ---------+---------+---------+---------+---------+---------+
      P  S  R  F  S  G  S  G  S  G  T  Q  Y  S  L  K  I  N  S  L

CAGTCTGAAGATTTTGGGAGTTATTACTGTCAACATTTTGGGGTACTCCGTACACGTTC
301 ---------+---------+---------+---------+---------+---------+
      Q  S  E  D  F  G  S  Y  Y  C  Q  H  F  W  G  T  P  Y  T  F

GGAGGGGGGACCAAGCTTGAAATAAAACGTGGTGGCGGGGGATCCGGCGGGGGAGGTTCA
361 ---------+---------+---------+---------+---------+---------+
      G  G  G  T  K  L  E  I  K  R  G  G  G  S  G  G  G  G  S

GGGGGTGGCGGATCCCAGGTTCAGCTGCAGCAGTCTGACGCTGAGTTGGTGAAACCTGGG
421 ---------+---------+---------+---------+---------+---------+
      G  G  G  G  S  Q  V  Q  L  Q  Q  S  D  A  E  L  V  K  P  G

GCTTCAGTGAAGATATCCTGCAAGGCTTCTGGCTACACCTTCACTGACCATGCTATTCAC
481 ---------+---------+---------+---------+---------+---------+
      A  S  V  K  I  S  C  K  A  S  G  Y  T  F  T  D  H  A  I  H

TGGGCGAAGCAGAAGCCTGAACAGGGCCTGGAATGGATTGGATATATTTCTCCCGGAAAT
541 ---------+---------+---------+---------+---------+---------+
      W  A  K  Q  K  P  E  Q  G  L  E  W  I  G  Y  I  S  P  G  N

GATGATATTAAGTACAATGAGAAGTTCAAGGGCAAGGCCACACTGACTGCAGACAAATCC
601 ---------+---------+---------+---------+---------+---------+
      D  D  I  K  Y  N  E  K  F  K  G  K  A  T  L  T  A  D  K  S

TCCAGCACTGCCTACATGCAGCTCAACAGCCTGACATCTGAGGATTCTGCAGTGTATTTC
661 ---------+---------+---------+---------+---------+---------+
      S  S  T  A  Y  M  Q  L  N  S  L  T  S  E  D  S  A  V  Y  F

TGTAAAAGATCGTACTACGGCCACTGGGGCCAAGGCACCACTCTCACAGTCTCCTCAGAG
721 ---------+---------+---------+---------+---------+---------+
      C  K  R  S  Y  Y  G  H  W  G  Q  G  T  T  L  T  V  S  S  E

TCCAAATATGGTCCCCCATGCCCATCAGCCCCATGATGA
781 ---------+---------+---------+---------+
      S  K  Y  G  P  P  C  P  S  A  P  *  *
```

Autoradiograph of SDS-PAGE of 125-Iodine labelled scFvhinge, disulphide linked dimer and cross-linked dimer.

1 2 3 4 5 6

1. Cross-linked dimer, reduced conditions
2. Disulphide linked dimer, reduced conditions
3. scFvh, reduced conditions
4. Cross-linked dimer, non-reduced conditions
5. Disulphide linked dimer, non-reduced conditions
6. scFvh, non-reduced conditions 1. Molecular weight markers at 97kDa, 67kDa, 43kDa, 30kDa, 20kDa and 14kDa.
2. scFvh
3. scFvh dimer cross-linking mix
4. scFvh (pRO97)
5. scFvh (pRO97) dimer cross-linking mix.

SDS-PAGE of scfvh Monomer, Dimer and Trimer

1. Molecular weight markers
   94, 67, 43, 30 & 20 kDa.
2. scFvh
3. scFvh dimer
4. scFvh trimer CX 76 : BIODISTRIBUTION AT 4H
125-I LABELLED SCFv : TRIMER v DIMER v MONOMER IN LS-174T TUMOUR-BEARING MICE.

REDUCING SDS-PAGE of scFvh Tetramer Cross-linking 1. scFvh
2. Tetramer cross-linking mix
3. Tetramer cross-linking mix

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
        ( A ) LENGTH: 474 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 16..468

( x i ) SEQUENCE DESCRIPTION: SEQ ID NO:1:

```
CCACTGACTC TAACC ATG GAA TGG AGC TGG GTC TTT CTC TTC TTC CTG TCA        51
                 Met Glu Trp Ser Trp Val Phe Leu Phe Phe Leu Ser
                  1               5                  10

GTA ACT ACA GGT GTC CAC TCC CAG GTT CAG CTG CAG CAG TCT GAC GCT         99
Val Thr Thr Gly Val His Ser Gln Val Gln Leu Gln Gln Ser Asp Ala
         15                  20                  25

GAG TTG GTG AAA CCT GGG GCT TCA GTG AAG ATA TCC TGC AAG GCT TCT        147
Glu Leu Val Lys Pro Gly Ala Ser Val Lys Ile Ser Cys Lys Ala Ser
     30                  35                  40

GGC TAC ACC TTC ACT GAC CAT GCT ATT CAC TGG GCG AAG CAG AAG CCT        195
Gly Tyr Thr Phe Thr Asp His Ala Ile His Trp Ala Lys Gln Lys Pro
 45                  50                  55                  60

GAA CAG GGC CTG GAA TGG ATT GGA TAT ATT TCT CCC GGA AAT GAT GAT        243
Glu Gln Gly Leu Glu Trp Ile Gly Tyr Ile Ser Pro Gly Asn Asp Asp
                 65                  70                  75

ATT AAG TAC AAT GAG AAG TTC AAG GGC AAG GCC ACA CTG ACT GCA GAC        291
Ile Lys Tyr Asn Glu Lys Phe Lys Gly Lys Ala Thr Leu Thr Ala Asp
             80                  85                  90

AAA TCC TCC AGC ACT GCC TAC ATG CAG CTC AAC AGC CTG ACA TCT GAG        339
Lys Ser Ser Ser Thr Ala Tyr Met Gln Leu Asn Ser Leu Thr Ser Glu
         95                  100                 105

GAT TCT GCA GTG TAT TTC TGT AAA AGA TCG TAC TAC GGC CAC TGG GGC        387
Asp Ser Ala Val Tyr Phe Cys Lys Arg Ser Tyr Tyr Gly His Trp Gly
     110                 115                 120

CAA GGC ACC ACT CTC ACA GTC TCC TCA GCT TCC ACC AAG GGC GAG TCC        435
Gln Gly Thr Thr Leu Thr Val Ser Ser Ala Ser Thr Lys Gly Glu Ser
125                 130                 135                 140

AAA TAT GGT CCC CCA TGC CCA TCA GCC CCA TGATGAATT                      474
Lys Tyr Gly Pro Pro Cys Pro Ser Ala Pro
                 145                 150
```

( 2 ) INFORMATION FOR SEQ ID NO:2:

( i ) SEQUENCE CHARACTERISTICS:
        ( A ) LENGTH: 150 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Glu Trp Ser Trp Val Phe Leu Phe Phe Leu Ser Val Thr Thr Gly
 1               5                  10                  15

Val His Ser Gln Val Gln Leu Gln Gln Ser Asp Ala Glu Leu Val Lys
             20                  25                  30

Pro Gly Ala Ser Val Lys Ile Ser Cys Lys Ala Ser Gly Tyr Thr Phe
         35                  40                  45

Thr Asp His Ala Ile His Trp Ala Lys Gln Lys Pro Glu Gln Gly Leu
     50                  55                  60

Glu Trp Ile Gly Tyr Ile Ser Pro Gly Asn Asp Asp Ile Lys Tyr Asn
```

|  | 65 |  |  |  | 70 |  |  |  | 75 |  |  |  | 80 |  |
| --- | --- | --- | --- | --- | --- | --- | --- | --- | --- | --- | --- | --- | --- | --- |
| Glu | Lys | Phe | Lys | Gly<br>85 | Lys | Ala | Thr | Leu | Thr<br>90 | Ala | Asp | Lys | Ser | Ser<br>95 | Ser |
| Thr | Ala | Tyr | Met<br>100 | Gln | Leu | Asn | Ser | Leu<br>105 | Thr | Ser | Glu | Asp | Ser<br>110 | Ala | Val |
| Tyr | Phe | Cys<br>115 | Lys | Arg | Ser | Tyr | Tyr<br>120 | Gly | His | Trp | Gly | Gln<br>125 | Gly | Thr | Thr |
| Leu | Thr<br>130 | Val | Ser | Ser | Ala | Ser<br>135 | Thr | Lys | Gly | Glu | Ser<br>140 | Lys | Tyr | Gly | Pro |
| Pro<br>145 | Cys | Pro | Ser | Ala | Pro<br>150 | | | | | | | | | | |

( 2 ) INFORMATION FOR SEQ ID NO:3:

( i ) SEQUENCE CHARACTERISTICS:
        ( A ) LENGTH: 819 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 1..816

( x i ) SEQUENCE DESCRIPTION: SEQ ID NO:3:

| AAA<br>Lys<br>1 | ATG<br>Met | AAA<br>Lys | AAG<br>Lys | ACA<br>Thr<br>5 | GCT<br>Ala | ATC<br>Ile | GCG<br>Ala | ATT<br>Ile | GCA<br>Ala<br>10 | GTG<br>Val | GCA<br>Ala | CTG<br>Leu | GCT<br>Ala | GGT<br>Gly<br>15 | TTC<br>Phe | 48 |
| --- | --- | --- | --- | --- | --- | --- | --- | --- | --- | --- | --- | --- | --- | --- | --- | --- |
| GCT<br>Ala | ACC<br>Thr | GTA<br>Val | GCG<br>Ala<br>20 | CAA<br>Gln | GCT<br>Ala | GAT<br>Asp | ATC<br>Ile | CAG<br>Gln<br>25 | ATG<br>Met | ACT<br>Thr | CAG<br>Gln | TCT<br>Ser | CCA<br>Pro<br>30 | GCC<br>Ala | TCC<br>Ser | 96 |
| CTA<br>Leu | TCT<br>Ser | GTA<br>Val<br>35 | TCT<br>Ser | GTG<br>Val | GGA<br>Gly | GAA<br>Glu | ACT<br>Thr<br>40 | GTC<br>Val | ACC<br>Thr | ATC<br>Ile | ACA<br>Thr | TGT<br>Cys<br>45 | CGA<br>Arg | GCA<br>Ala | AGT<br>Ser | 144 |
| GAG<br>Glu | AAT<br>Asn<br>50 | ATT<br>Ile | TAC<br>Tyr | AGT<br>Ser | AAT<br>Asn | TTA<br>Leu<br>55 | GCA<br>Ala | TGG<br>Trp | TAT<br>Tyr | CAA<br>Gln | CAG<br>Gln<br>60 | AAA<br>Lys | CAG<br>Gln | GGA<br>Gly | AAA<br>Lys | 192 |
| TCT<br>Ser<br>65 | CCT<br>Pro | CAG<br>Gln | CTC<br>Leu | CTG<br>Leu | GTC<br>Val<br>70 | TAT<br>Tyr | GCT<br>Ala | GCA<br>Ala | ACA<br>Thr | AAC<br>Asn<br>75 | TTA<br>Leu | GCA<br>Ala | GAT<br>Asp | GGT<br>Gly | GTG<br>Val<br>80 | 240 |
| CCA<br>Pro | TCA<br>Ser | AGG<br>Arg | TTC<br>Phe | AGT<br>Ser<br>85 | GGC<br>Gly | AGT<br>Ser | GGA<br>Gly | TCG<br>Ser | GGC<br>Gly<br>90 | ACA<br>Thr | CAG<br>Gln | TAT<br>Tyr | TCC<br>Ser | CTC<br>Leu<br>95 | AAG<br>Lys | 288 |
| ATC<br>Ile | AAC<br>Asn | AGC<br>Ser | CTG<br>Leu<br>100 | CAG<br>Gln | TCT<br>Ser | GAA<br>Glu | GAT<br>Asp | TTT<br>Phe<br>105 | GGG<br>Gly | AGT<br>Ser | TAT<br>Tyr | TAC<br>Tyr | TGT<br>Cys<br>110 | CAA<br>Gln | CAT<br>His | 336 |
| TTT<br>Phe | TGG<br>Trp | GGT<br>Gly<br>115 | ACT<br>Thr | CCG<br>Pro | TAC<br>Tyr | ACG<br>Thr | TTC<br>Phe<br>120 | GGA<br>Gly | GGG<br>Gly | GGG<br>Gly | ACC<br>Thr | AAG<br>Lys<br>125 | CTT<br>Leu | GAA<br>Glu | ATA<br>Ile | 384 |
| AAA<br>Lys | CGT<br>Arg<br>130 | GGT<br>Gly | GGC<br>Gly | GGG<br>Gly | GGA<br>Gly | TCC<br>Ser<br>135 | GGC<br>Gly | GGG<br>Gly | GGA<br>Gly | GGT<br>Gly | TCA<br>Ser<br>140 | GGG<br>Gly | GGT<br>Gly | GGC<br>Gly | GGA<br>Gly | 432 |
| TCC<br>Ser<br>145 | CAG<br>Gln | GTT<br>Val | CAG<br>Gln | CTG<br>Leu | CAG<br>Gln<br>150 | CAG<br>Gln | TCT<br>Ser | GAC<br>Asp | GCT<br>Ala | GAG<br>Glu<br>155 | TTG<br>Leu | GTG<br>Val | AAA<br>Lys | CCT<br>Pro | GGG<br>Gly<br>160 | 480 |
| GCT<br>Ala | TCA<br>Ser | GTG<br>Val | AAG<br>Lys | ATA<br>Ile<br>165 | TCC<br>Ser | TGC<br>Cys | AAG<br>Lys | GCT<br>Ala | TCT<br>Ser<br>170 | GGC<br>Gly | TAC<br>Tyr | ACC<br>Thr | TTC<br>Phe | ACT<br>Thr<br>175 | GAC<br>Asp | 528 |
| CAT<br>His | GCT<br>Ala | ATT<br>Ile | CAC<br>His<br>180 | TGG<br>Trp | GCG<br>Ala | AAG<br>Lys | CAG<br>Gln | AAG<br>Lys<br>185 | CCT<br>Pro | GAA<br>Glu | CAG<br>Gln | GGC<br>Gly | CTG<br>Leu<br>190 | GAA<br>Glu | TGG<br>Trp | 576 |

| | | | | | | | | | | | | | | | | |
|---|---|---|---|---|---|---|---|---|---|---|---|---|---|---|---|---|
| ATT | GGA | TAT | ATT | TCT | CCC | GGA | AAT | GAT | GAT | ATT | AAG | TAC | AAT | GAG | AAG | 624 |
| Ile | Gly | Tyr | Ile | Ser | Pro | Gly | Asn | Asp | Asp | Ile | Lys | Tyr | Asn | Glu | Lys | |
| | 195 | | | | | 200 | | | | | 205 | | | | | |
| TTC | AAG | GGC | AAG | GCC | ACA | CTG | ACT | GCA | GAC | AAA | TCC | TCC | AGC | ACT | GCC | 672 |
| Phe | Lys | Gly | Lys | Ala | Thr | Leu | Thr | Ala | Asp | Lys | Ser | Ser | Ser | Thr | Ala | |
| 210 | | | | | 215 | | | | | 220 | | | | | | |
| TAC | ATG | CAG | CTC | AAC | AGC | CTG | ACA | TCT | GAG | GAT | TCT | GCA | GTG | TAT | TTC | 720 |
| Tyr | Met | Gln | Leu | Asn | Ser | Leu | Thr | Ser | Glu | Asp | Ser | Ala | Val | Tyr | Phe | |
| 225 | | | | | 230 | | | | | 235 | | | | | 240 | |
| TGT | AAA | AGA | TCG | TAC | TAC | GGC | CAC | TGG | GGC | CAA | GGC | ACC | ACT | CTC | ACA | 768 |
| Cys | Lys | Arg | Ser | Tyr | Tyr | Gly | His | Trp | Gly | Gln | Gly | Thr | Thr | Leu | Thr | |
| | | | | 245 | | | | | 250 | | | | | 255 | | |
| GTC | TCC | TCA | GAG | TCC | AAA | TAT | GGT | CCC | CCA | TGC | CCA | TCA | GCC | CCA | TGATGA | 819 |
| Val | Ser | Ser | Glu | Ser | Lys | Tyr | Gly | Pro | Pro | Cys | Pro | Ser | Ala | Pro | | |
| | | | 260 | | | | | 265 | | | | | 270 | | | |

( 2 ) INFORMATION FOR SEQ ID NO:4:

( i ) SEQUENCE CHARACTERISTICS:
        ( A ) LENGTH: 271 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| | | | | | | | | | | | | | | |
|---|---|---|---|---|---|---|---|---|---|---|---|---|---|---|
| Lys | Met | Lys | Lys | Thr | Ala | Ile | Ala | Ile | Ala | Val | Ala | Leu | Ala | Gly | Phe |
| 1 | | | | 5 | | | | | 10 | | | | | 15 | |
| Ala | Thr | Val | Ala | Gln | Ala | Asp | Ile | Gln | Met | Thr | Gln | Ser | Pro | Ala | Ser |
| | | | 20 | | | | | 25 | | | | | 30 | | |
| Leu | Ser | Val | Ser | Val | Gly | Glu | Thr | Val | Thr | Ile | Thr | Cys | Arg | Ala | Ser |
| | | | 35 | | | | | 40 | | | | | 45 | | |
| Glu | Asn | Ile | Tyr | Ser | Asn | Leu | Ala | Trp | Tyr | Gln | Gln | Lys | Gln | Gly | Lys |
| | 50 | | | | | 55 | | | | | 60 | | | | |
| Ser | Pro | Gln | Leu | Leu | Val | Tyr | Ala | Ala | Thr | Asn | Leu | Ala | Asp | Gly | Val |
| 65 | | | | | 70 | | | | | 75 | | | | | 80 |
| Pro | Ser | Arg | Phe | Ser | Gly | Ser | Gly | Ser | Gly | Thr | Gln | Tyr | Ser | Leu | Lys |
| | | | | 85 | | | | | 90 | | | | | 95 | |
| Ile | Asn | Ser | Leu | Gln | Ser | Glu | Asp | Phe | Gly | Ser | Tyr | Tyr | Cys | Gln | His |
| | | | 100 | | | | | 105 | | | | | 110 | | |
| Phe | Trp | Gly | Thr | Pro | Tyr | Thr | Phe | Gly | Gly | Gly | Thr | Lys | Leu | Glu | Ile |
| | | 115 | | | | | 120 | | | | | 125 | | | |
| Lys | Arg | Gly | Gly | Gly | Gly | Ser | Gly | Gly | Gly | Gly | Ser | Gly | Gly | Gly | Gly |
| | | 130 | | | | 135 | | | | | 140 | | | | |
| Ser | Gln | Val | Gln | Leu | Gln | Gln | Ser | Asp | Ala | Glu | Leu | Val | Lys | Pro | Gly |
| 145 | | | | 150 | | | | | 155 | | | | | 160 | |
| Ala | Ser | Val | Lys | Ile | Ser | Cys | Lys | Ala | Ser | Gly | Tyr | Thr | Phe | Thr | Asp |
| | | | 165 | | | | | 170 | | | | | 175 | | |
| His | Ala | Ile | His | Trp | Ala | Lys | Gln | Lys | Pro | Glu | Gln | Gly | Leu | Glu | Trp |
| | | | 180 | | | | | 185 | | | | | 190 | | |
| Ile | Gly | Tyr | Ile | Ser | Pro | Gly | Asn | Asp | Asp | Ile | Lys | Tyr | Asn | Glu | Lys |
| | | 195 | | | | | 200 | | | | | 205 | | | |
| Phe | Lys | Gly | Lys | Ala | Thr | Leu | Thr | Ala | Asp | Lys | Ser | Ser | Ser | Thr | Ala |
| | 210 | | | | | 215 | | | | | 220 | | | | |
| Tyr | Met | Gln | Leu | Asn | Ser | Leu | Thr | Ser | Glu | Asp | Ser | Ala | Val | Tyr | Phe |
| 225 | | | | | 230 | | | | | 235 | | | | | 240 |
| Cys | Lys | Arg | Ser | Tyr | Tyr | Gly | His | Trp | Gly | Gln | Gly | Thr | Thr | Leu | Thr |
| | | | | 245 | | | | | 250 | | | | | 255 | |

Val Ser Ser Glu Ser Lys Tyr Gly Pro Pro Cys Pro Ser Ala Pro
260                 265                 270

(2) INFORMATION FOR SEQ ID NO:5:

(i) SEQUENCE CHARACTERISTICS:
        (A) LENGTH: 17 amino acids
        (B) TYPE: amino acid
        (D) TOPOLOGY: linear (xi) SEQUENCE DESCRIPTION: SEQ ID NO:5:

Ala Ser Thr Lys Gly Glu Ser Lys Tyr Gly Pro Pro Cys Pro Ser Ala
1               5                   10                  15

Pro (2) INFORMATION FOR SEQ ID NO:6:

(i) SEQUENCE CHARACTERISTICS:
        (A) LENGTH: 17 amino acids
        (B) TYPE: amino acid
        (D) TOPOLOGY: linear (xi) SEQUENCE DESCRIPTION: SEQ ID NO:6:

Ala Ser Thr Lys Gly Glu Arg Lys Cys Cys Val Glu Cys Pro Pro Cys
1               5                   10                  15

Pro (2) INFORMATION FOR SEQ ID NO:7:

(i) SEQUENCE CHARACTERISTICS:
        (A) LENGTH: 21 amino acids
        (B) TYPE: amino acid
        (D) TOPOLOGY: linear (xi) SEQUENCE DESCRIPTION: SEQ ID NO:7:

Ala Ser Thr Lys Gly Glu Leu Lys Thr Pro Leu Gly Thr Thr His Thr
1               5                   10                  15

Cys Pro Arg Cys Pro
                20

(2) INFORMATION FOR SEQ ID NO:8:

(i) SEQUENCE CHARACTERISTICS:
        (A) LENGTH: 35 amino acids
        (B) TYPE: amino acid
        (D) TOPOLOGY: linear (xi) SEQUENCE DESCRIPTION: SEQ ID NO:8:

Ala Ser Thr Lys Gly Glu Leu Lys Thr Pro Leu Gly Thr Thr His Thr
1               5                   10                  15

Cys Pro Arg Cys Pro Glu Pro Lys Ser Cys Asp Thr Pro Pro Pro Cys
                20                  25                  30

Arg Cys Pro
35

(2) INFORMATION FOR SEQ ID NO:9:

(i) SEQUENCE CHARACTERISTICS:
        (A) LENGTH: 49 amino acids
        (B) TYPE: amino acid
        (D) TOPOLOGY: linear (xi) SEQUENCE DESCRIPTION: SEQ ID NO:9:

Ala Ser Thr Lys Gly Glu Leu Lys Thr Pro Leu Gly Thr Thr His Thr
1               5                   10                  15

```
Cys  Pro  Arg  Cys  Pro  Glu  Pro  Lys  Ser  Cys  Asp  Thr  Pro  Pro  Pro  Cys
               20                       25                         30

Arg  Cys  Pro  Glu  Pro  Lys  Ser  Cys  Asp  Thr  Pro  Pro  Pro  Cys  Arg  Cys
               35                       40                         45

Pro
```

( 2 ) INFORMATION FOR SEQ ID NO:10:

( i ) SEQUENCE CHARACTERISTICS:
        ( A ) LENGTH: 63 amino acids
        ( B ) TYPE: amino acid
        ( D ) TOPOLOGY: linear ( x i ) SEQUENCE DESCRIPTION: SEQ ID NO:10:

```
Ala  Ser  Thr  Lys  Gly  Glu  Leu  Lys  Thr  Pro  Leu  Gly  Thr  Thr  His  Thr
 1                        5                        10                        15

Cys  Pro  Arg  Cys  Pro  Glu  Pro  Lys  Ser  Cys  Asp  Thr  Pro  Pro  Pro  Cys
               20                       25                         30

Arg  Cys  Pro  Glu  Pro  Lys  Ser  Cys  Asp  Thr  Pro  Pro  Pro  Cys  Arg  Cys
               35                       40                         45

Pro  Glu  Pro  Lys  Ser  Cys  Asp  Thr  Pro  Pro  Pro  Cys  Arg  Cys  Pro
      50                       55                         60
```

( 2 ) INFORMATION FOR SEQ ID NO:11:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

GGGCCAAGGC ACCACTCTCA CAGTCTC                                                          27

( 2 ) INFORMATION FOR SEQ ID NO:12:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i v ) ANTI-SENSE: YES ( x i ) SEQUENCE DESCRIPTION: SEQ ID NO:12:

TGAGGAGACT GTGAGAGTGG TGCCTTGGCC CCAG                                                  34

( 2 ) INFORMATION FOR SEQ ID NO:13:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

CTCAGCTTCC ACCAAGGGCG AGTCCAAATA TGGTCC                                                36

( 2 ) INFORMATION FOR SEQ ID NO:14:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear (i v) ANTI-SENSE: YES (x i) SEQUENCE DESCRIPTION: SEQ ID NO:14:

TGGGGGAACC ATATTTGGAC TCGCCCTTGG TGGAAGC      37

(2) INFORMATION FOR SEQ ID NO:15:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (x i) SEQUENCE DESCRIPTION: SEQ ID NO:15:

CCCATGCCCA TCAGCCCCAT GATG      24

(2) INFORMATION FOR SEQ ID NO:16:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i v) ANTI-SENSE: YES (x i) SEQUENCE DESCRIPTION: SEQ ID NO:16:

AATTCATCAT GGGGCTGATG GGCA      24

(2) INFORMATION FOR SEQ ID NO:17:

(i) SEQUENCE CHARACTERISTICS:
        (A) LENGTH: 17 amino acids
        (B) TYPE: amino acid
        (D) TOPOLOGY: linear (x i) SEQUENCE DESCRIPTION: SEQ ID NO:17:

Ala Ser Thr Lys Gly Glu Ser Lys Tyr Gly Pro Pro Cys Pro Ser Ala
1               5                   10                  15
Pro (2) INFORMATION FOR SEQ ID NO:18:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (x i) SEQUENCE DESCRIPTION: SEQ ID NO:18:

AGCTTGAAAT AAAACGTGGT GGCGGGGGAT CCGGCGGGGG AGGTTCAGGG GGTGGCGGAT      60

CCCAGGTTCA G      71

(2) INFORMATION FOR SEQ ID NO:19:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (i v) ANTI-SENSE: YES (x i) SEQUENCE DESCRIPTION: SEQ ID NO:19:

CTGAACCTGG GATCCGCCAC CCCCTGAACC TCCCCCGCCG GATCCCCGC CACCACGTTT      60

TATTTCA 67

( 2 ) INFORMATION FOR SEQ ID NO:20:

( i ) SEQUENCE CHARACTERISTICS:
        ( A ) LENGTH: 84 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 1..84

( x i ) SEQUENCE DESCRIPTION: SEQ ID NO:20:

```
ACC  AAG  CTT  GAA  ATA  AAA  CGT  GGT  GGC  GGG  GGA  TCC  GGC  GGG  GGA  GGT    48
Thr  Lys  Leu  Glu  Ile  Lys  Arg  Gly  Gly  Gly  Gly  Ser  Gly  Gly  Gly  Gly
 1                   5                        10                       15

TCA  GGG  GGT  GGC  GGA  TCC  CAG  GTT  CAG  CTG  CAG  CAG                        84
Ser  Gly  Gly  Gly  Gly  Ser  Gln  Val  Gln  Leu  Gln  Gln
              20                        25
```

( 2 ) INFORMATION FOR SEQ ID NO:21:

( i ) SEQUENCE CHARACTERISTICS:
        ( A ) LENGTH: 28 amino acids
        ( B ) TYPE: amino acid
        ( D ) TOPOLOGY: linear ( i i ) MOLECULE TYPE: protein ( x i ) SEQUENCE DESCRIPTION: SEQ ID NO:21:

```
Thr  Lys  Leu  Glu  Ile  Lys  Arg  Gly  Gly  Gly  Gly  Ser  Gly  Gly  Gly  Gly
 1                   5                        10                       15

Ser  Gly  Gly  Gly  Gly  Ser  Gln  Val  Gln  Leu  Gln  Gln
              20                        25
```

( 2 ) INFORMATION FOR SEQ ID NO:22:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

CCCCCCCTCG AGTTCTAGAT AACGA 25

( 2 ) INFORMATION FOR SEQ ID NO:23:

( i ) SEQUENCE CHARACTERISTICS:
        ( A ) LENGTH: 78 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

GCGCGAATTC ATCATGGGGC TTGATGGGCA TGGGGGACCA TATTTGGACT CTGAGGAGAC 60

TGTGAGAGTG GTGCCTTG 78

( 2 ) INFORMATION FOR SEQ ID NO:24:

( i ) SEQUENCE CHARACTERISTICS:
        ( A ) LENGTH: 17 amino acids
        ( B ) TYPE: amino acid
        ( D ) TOPOLOGY: linear ( x i ) SEQUENCE DESCRIPTION: SEQ ID NO:24:

(2) INFORMATION FOR SEQ ID NO:25:

(i) SEQUENCE CHARACTERISTICS:
        (A) LENGTH: 17 amino acids
        (B) TYPE: amino acid
        (D) TOPOLOGY: linear (xi) SEQUENCE DESCRIPTION: SEQ ID NO:25:

```
Ala Ser Thr Thr Gly Glu Ser Lys Tyr Gly Pro Pro Cys Pro Ser Ala
1               5                   10                  15
Pro
```

(2) INFORMATION FOR SEQ ID NO:26:

(i) SEQUENCE CHARACTERISTICS:
        (A) LENGTH: 17 amino acids
        (B) TYPE: amino acid
        (D) TOPOLOGY: linear (xi) SEQUENCE DESCRIPTION: SEQ ID NO:26:

```
Ala Ser Thr Thr Gly Glu Ser Thr Tyr Gly Pro Pro Cys Pro Ser Ala
1               5                   10                  15
Pro
```

MULTIVALENT ANTIGEN-BINDING PROTEINS

This application is a continuation of 08/127,136 filed Sep. 27, 1993, now abandoned, which is a continuation of 07/842,193 filed Mar. 17, 1992, now abandoned, which was filed as a national stage application under 35 USC § 371 from PCT/GB91/00935 which was filed Jun. 11, 1991.

FIELD OF THE INVENTION

The present invention relates to multivalent antigen-binding proteins and to methods for their production. The invention relates in particular, but not exclusively, to the use of recombinant DNA technology to produce such multivalent antigen-binding proteins.

BACKGROUND OF THE INVENTION

There has been much interest in recent years in antibodies and their fragments. It is well known that complete antibody molecules comprise four polypeptide chains, two heavy chains and two light chains. Each light chain consists of two domains, the N-terminal domain being known as the variable or VL domain and the C-terminal domain being known as the constant or CL domain. Each heavy chain consists of four or five domains, depending on the class of the antibody. The N-terminal domain is known as the variable or VH domain. The next domain is known as the first constant or CH1 domain. The next part of each heavy chain is known as the hinge region and this is then followed by the second, third and, in some cases, fourth constant or CH2, CH3 and CH4 domains respectively.

In an assembled antibody, the VL and VH domains associate together to form an antigen binding site. Also the CL and CH1 domains associate together to keep one heavy chain associated with one light chain. The two heavy-light chain heterodimers associate together partly by interaction of the CH2, CH3 and CH4 domains of the two heavy chains and partly because of interaction between the hinge regions on the two heavy chains.

Each heavy chain hinge region includes at least one, and often several, cysteine residues. In the assembled antibody, the cysteine residues in the heavy chains are aligned so that disulphide bonds can be formed between the cysteine residues in the hinge regions covalently bonding the two heavy-light chain heterodimers together. Thus, fully assembled antibodies are bivalent in that they have two antigen binding sites.

It has been known for some long time that if the disulphide bonds in an antibody's hinge region are broken by mild reduction, it is possible to produce a monovalent antibody comprising a single heavy-light chain heterodimer.

It has also been known for some long time that treatment of antibodies with certain proteolytic enzymes leads to the production of various antibody fragments. For instance, if an antibody is cleaved close to the N-terminal side of each hinge region, two antibody binding fragments (Fab) and one constant region fragment (Fc) are produced. Each Fab fragment comprises the light chain associated with a truncated heavy chain comprising only the VH and CH1 domains. The Fc portion comprises the remaining domains of the heavy chains held together by the hinge region.

Alternatively, the antibody may be cleaved close to the C-terminal side of the hinge. This produces a fragment known as the $F(ab)_2$ fragment. This essentially comprises two Fab fragments but with the CH1 domains still attached to the hinge regions. Thus, the $F(ab)_2$ fragment is a bivalent fragment having the two antigen binding sites linked together by the hinge region.

It has also proved to be possible, by careful control of digestion conditions, to cleave an antibody between the VL and CL and between the VH and CH1 domains. This gives rise to two fragments known as FV fragments. Each Fv fragment comprises a VL and a VE domain associated with one another. Each Fv fragment is monovalent for antigen binding.

In more recent years, there has been much interest in producing antibodies or their fragments by use of recombinant DNA technology. The patent literature is replete with disclosures in this area. Recombinant DNA technology has been used not only to reproduce natural antibodies but also to produce novel antibodies. For instance, it is now possible to produce chimeric antibodies, wherein the variable domains from one species are linked to constant domains from another species.

It is also possible to produce CDR-grafted antibodies, in which the regions in the VH and VL domains responsible for antigen binding activity (usually referred to as the Complementarity Determining Regions) have been changed in sequence so that a different antigen can be bound. CDR-grafting an antibody is a useful procedure in that it allows a specificity from, for instance, a mouse monoclonal antibody to be transferred to a human antibody without altering the essentially human nature of the antibody. This has advantages where it is desired to use the antibody in vivo.

Relatively recently, there has been interest in producing Fv fragments by recombinant DNA technology. For instance, production of Fv fragments by recombinant DNA technology has been suggested by Skerra and Pluckthun [1]. (A list of references is appended at the end of the description.) The production of Fv-producing recombinant host cells has been described in published International patent application Ser. Nos. WO 89/02465 and WO 89/09825.

It is envisaged that Fv fragments will be of particular use in in vivo diagnosis and in therapy because of their small size as compared to Fab fragments or complete antibodies. This will mean that they are likely to be less antigenic and more able to penetrate tissue. In particular, it is envisaged that they may be able to penetrate cancerous tissue and therefore deliver a cytotoxic drug or diagnostic label to the site of the cancer.

Fv fragments have the disadvantage that they are monovalent with respect to antigen binding. Most naturally occurring antigens are multivalent, i.e. they display multiple antigenic determinants. Therefore, the Fv fragments, with only one antigen binding site per molecule, will bind to such antigens less strongly than the bivalent whole antibody or an $F(ab)_2$ fragment. This may reduce the usefulness of the Fv fragment, for example in targeting a cell surface antigen.

SUMMARY OF THE INVENTION

According to the present invention, there is provided a multivalent antigen-binding protein comprising a first Fv fragment bound to at least one further Fv fragment by a connecting structure which links the Fv fragments to each other but which maintains them spaced apart such that the protein is capable of binding to adjacent antigenic determinants.

Characteristically the connecting structure which links the FV fragments to each other does not consist of CL, CH1 and heavy chain hinge region as in a $F(ab)_2$ fragment or complete antibody molecule.

DETAILED DESCRIPTION OF THE INVENTION

The two Fv fragments may be bound together either covalently or non-covalently.

It is important for the connecting structure to serve two functions. Firstly, it must keep the Fv fragments associated. Secondly, it must keep the Fv fragments spaced from one another. If this is not done, it may not be possible for the antigen-binding protein to assemble. Even if it can, the close proximity of the fragments may cause steric interference at the binding site, thus preventing the antigen-binding protein having any antigen binding activity.

Preferably, the connecting structure consists of two elements, a spacing polypeptide sequence, advantageously at the one end of one of the VH and VL domains, and a linkage unit. Preferably., the spacing polypeptide sequence is at the C-terminal end of the domain, which is advantageously the VH domain. In general, the spacing polypeptide sequence will be about 3 to 16, preferably about 7 to 12 or especially about 10 amino acid residues in length although shorter or longer sequences could be used depending on the Fv fragment used and the remainder of the connecting structure.

Preferably, also, the connecting structure is sufficiently flexible to permit the FV fragments to flex in relation to one another. Thus the connecting structure preferably is not composed of large insoluble amino acid residues or tight helix-forming sequences of amino acids. Preferably, the amino acid residues of the connecting structure comprise relatively small and soluble amino acid residues.

The spacing polypeptide sequence may have towards, or at, its C-terminal end one or more linkable residues which can be used for attachment of a linkage unit. For instance, the linkable residue may be a cysteine, a lysine, glutamic acid or aspartic acid residue. In these cases, the linkage unit will preferably contain a thiol, carboxyl or amino group for reaction with the linkable residue.

The linkage unit may be a specifically designed chemical compound, such as 1,6 bismaleimidohexane, which will cross link between thiol groups, or a cyclic polypeptide, for instance containing a number of lysine residues to which aspartic or glutamic acid residues can link. In the latter case, it will be possible to produce multivalent antigen-binding proteins by linking a VE-VL dimer to each reactive residue in the cyclic polypeptide. Also, tri-, tetra- or higher multifuctional maleimide linkers may be used for the tri-, tetra- and higher multivalent products. Such multivalent maleimide linkers are described in our British patent application entitled "Chemical Compounds" corresponding to PCT published application Ser. No. WO 92/22583, filed in the U.S. as Ser. No. 08/232,401 filed on even date herewith. Alternatively, multivalent proteins may be produced by linking VH-VL dimers to multifunctional support structures, such as polymer beads.

Alternatively, the linkage unit may be a molecule which allows for non-covalent binding such as electrostatic or other binding. For instance, the linkage unit may comprise the biotin-streptavidin complex. The biotin molecule would be linked to one Fv fragment by the spacing polypeptide. The streptavidin molecule would be linked to another Fv fragment by the spacing peptide. Mixing of the two Fv fragments would lead to non-covalent association of the biotin and streptavidin, thus forming bivalent antigen-binding proteins. It will be appreciated that other non-covalently associating pairs of molecules could be used in place of the biotin-streptavidin complex.

Preferably, the spacing polypeptide leads directly into a polypeptide sequence which forms the linkage unit. For instance, it would be possible to have as the linkage unit a protein which has a known affinity for a second protein, or for itself. In this case, one of the chains in the Fv could comprise the Fv polypeptide sequence fused to a spacing sequence which in turn is fused to the protein sequence. Alternatively, the linkage unit may comprise a peptide sequence rich in residues which can be covalently linked together, such as lysine, cysteine or aspartic or glutamic acid residues. Preferably, the linkage unit is rich in cysteine residues.

It is known that, in assembled antibodies, there is a polypeptide sequence which joins the VH domain to the CH1 domain. Similarly, there is such a joining sequence connecting the VL and CL domains. These joining sequences are generally about five amino acid residues in length. Preferably, one of these joining sequences is used as at least part of the spacing polypeptide sequence. In some instances, it may be possible to use only a joining sequence as the spacing sequence.

Advantageously, the linkage unit comprises the core section of an antibody hinge region. It is known that the hinge region of an antibody comprises a polypeptide sequence having a core section which is rich in proline a cysteine residues. On the N-terminal and C-terminal sides of the core section are polypeptide sequences which are not directly involved in the linkage between the cysteine residues, but which are not part of the CH1 or CH2 domains flanking the hinge.

The core section of an antibody hinge by itself may be used as the linkage unit. Alternatively, the linkage unit may comprise a number of identical core units and/or parts thereof in sequence.

Where the spacing unit is formed in part by a joining sequence, the remainder of the spacing sequence is preferably formed by the N-terminal part of the hinge region.

Thus, a presently preferred multivalent antigen-binding protein according to the present invention comprises a VH domain having attached to its C-terminal end a joining sequence and an antibody hinge sequence. The VH domain will be associated with a VL domain and the VH-VL heterodimer will be linked to a similar VH-VL heterodimer by disulphide bonds formed between the hinge region cysteine residues.

Particularly preferred connecting structures, based on antibody joining and hinge region sequences have the amino acid sequences given below (using the conventional single letter amino acid code).

A S T K G E S K Y G / P P C P S A P SEQ ID NO:5
A S T K G E R K / C C V E C P P C P SEQ ID NO:6
A S T K G E L K T / P L G T T H T C P R C P (E P K S C D T P P P C R C P)$_n$ (wherein n=0 to 3). SEQ ID NO:7 is when n=0, SEQ ID NO:8 is when n=1, SEQ ID NO:9 is when n=2, and SEQ ID NO:10 is when n=3.

The slanted line indicates approximately the boundary between the spacing sequence and the hinge core section. Appropriate analogues and variants of such sequences are also included within the invention.

It will be appreciated that the multivalent antigen-binding protein of the present invention may have only one specificity, where the VH-VL heterodimers in the protein are identical, or may have multiple specificities. A multispecific antigen-binding protein will be useful, for instance, in cases where it is known that a first desired antigen is only sparsely present on a cell surface but in combination with a second desired antigen. If a monospecific protein were used, it might not be possible to obtain avid binding to the antigen. However, if it were known that the cell surface had present the second antigen, it would be possible to make the antigen-binding protein bispecific for the two antigens, thus ensuring that it avidly bound to the desired target cell.

It will also be appreciated that the VH or VL domains may have a natural sequence, an altered sequence or a CDR-grafted sequence. For example the VH and VL domains may comprise human framework regions and non-human (e.g. mouse monoclonal) CDRs. Also, for example, the VH and/or VL domains may contain specific altered residues, e.g. cysteine, lysine, aspartic acid or glutamic acid residues, to enable cross-linking between the VH and VL domains. The present invention encompasses multivalent antigen-binding proteins with any such sequence variation.

It will be further appreciated that the multivalent antigen-binding proteins of the present invention, or at least parts thereof, will best be produced by use of recombinant DNA technology. For instance, each domain of the protein can be expressed separately in a host cell. One domain will be essentially only as long as a natural domain (although it may include sequence changes as discussed above). The other domain will preferably have on one end at least a spacing and most preferably a spacing sequence and a linkage unit sequence.

Advantageously, the VH and VL domain polypeptides are coexpressed in a single host cell. The genes encoding the domains may be on separate, but compatible, vectors, or may be on the same vector. If an appropriate host cell is chosen, the two domains may associate correctly and the VH-VL heterodimers may then assemble to form a bivalent or multivalent antigen-binding protein.

If the two domains do not associate correctly on expression or if the VH-VL heterodimers do not assemble, it will be necessary to take appropriate steps to cause formation of the bi- or multivalent antigen binding protein, such as de- and re-naturation or partial reduction and reoxidation of disulphide bonds.

Alternatively, in a particularly preferred embodiment, the two variable domains (VH and VL) may be linked by a peptide to form a single chain polypeptide expressed by a vector in a single host cell, i.e. a single chain Fv (scFv). The multivalent protein advantageously comprises one or more single chain Fvs.

According to further particularly preferred aspects of the present invention, there are provided:

(a) an antibody variable domain, preferably a VH domain, having fused onto one of its ends, preferably its C-terminal end, a spacing polypeptide sequence;

(b) the polypeptide sequence as described in (a) having additionally a linkage unit comprising a polypeptide sequence fused to the end of the spacing sequence remote from the variable domain;

(c) methods for producing the polypeptide sequences as described in (a) or (b) above by use of recombinant DNA technology; and (d) a method of producing a bivalent (or higher multivalent) antigen-binding protein by recombinant DNA technology comprising the steps of:

(i) preparing a gene encoding a polypeptide sequence as described in (a) above;

(ii) preparing a gene encoding a variable domain complementary to the variable domain encoded by the gene prepared in step (i);

(iii) transforming a host cell with the two genes, either on the same vector or on separate vectors; and (iv) causing the cell to express the polypeptides encoded by the genes, preferably under such conditions that the desired bivalent (or higher multivalent) antigen-binding protein is correctly assembled.

If the conditions in step (iv) above cannot be arranged to promote correct assembly, it will be necessary to carry out a step (v) of assembling the desired bivalent (or higher multivalent) antigen-binding protein from the expressed polypeptides.

It will be appreciated that a wide range of cell lines, vectors and recombinant DNA procedures may be used to put this invention into effect. A skilled person will readily be able to carry out the necessary manipulations using the ordinary knowledge and generally available materials of the art. However, it is preferred that bacterial, and in particular *E. coli* host cells are used in connection with the present invention.

The multivalent antigen-binding proteins of the invention may be used among other things for in vivo diagnosis or therapy.

Thus the invention also includes multivalent antigen-binding proteins according to the invention having attached thereto diagnostically or therapeutically functional effector molecules, atoms or other species.

For example, the protein may have a radioactive diagnostic label or radioactive cytotoxic atom or metal or cytotoxic species, e.g. ricin chain, attached thereto for in vivo diagnosis or therapy of cancer. The diagnostically or therapeutically functional effector species may be attached to the protein in any suitable position, though is preferably attached to the connecting structure, either the spacing polypeptide or preferably the linkage unit. The proteins of the invention are believed to be particularly suited for in vivo diagnostic purposes in view of their relatively quick clearance from the blood stream coupled with the relatively high signal to noise ratio which may be achieved when labelling specific sites, such as tumours.

Thus the invention also includes diagnostic or therapeutic compositions for in vivo use comprising an effective amount of a protein according to the invention in combination with a pharmaceutically acceptable diluent, carrier or excipient.

Moreover, the invention includes methods of diagnosis or therapy comprising administering an effective amount of a protein of the invention to a human or animal subject.

The present invention is now described, by way of example only, with reference to the accompanying drawings, in which:

BRIEF DESCRIPTION OF THE DRAWINGS

FIGS. 1A and FIG. 1B show the nucleotide sequence (SEQ ID NO:1) encoding, and the amino acid sequence (SEQ ID NO:2) of, a polypeptide chain comprising, fused together in the order given, a leader sequence (amino acid residues 1 to 19), the B72.3 VH domain (amino acid residues 20 to 114) and a connecting structure (amino acid residue 115 to 132);

FIG. 5 shows the nucleotide sequence (SEQ ID NO:3) encoding, and the amino acid sequence (SEQ ID NO:4) of the shortened hinge version of the B72.3 single chain Fv hinge (scFvhinge) construct of plasmid pRO97;

EXAMPLES OF THE INVENTION

EXAMPLE 1

Bivalent B72.3 Fv Product

Figure 2A:
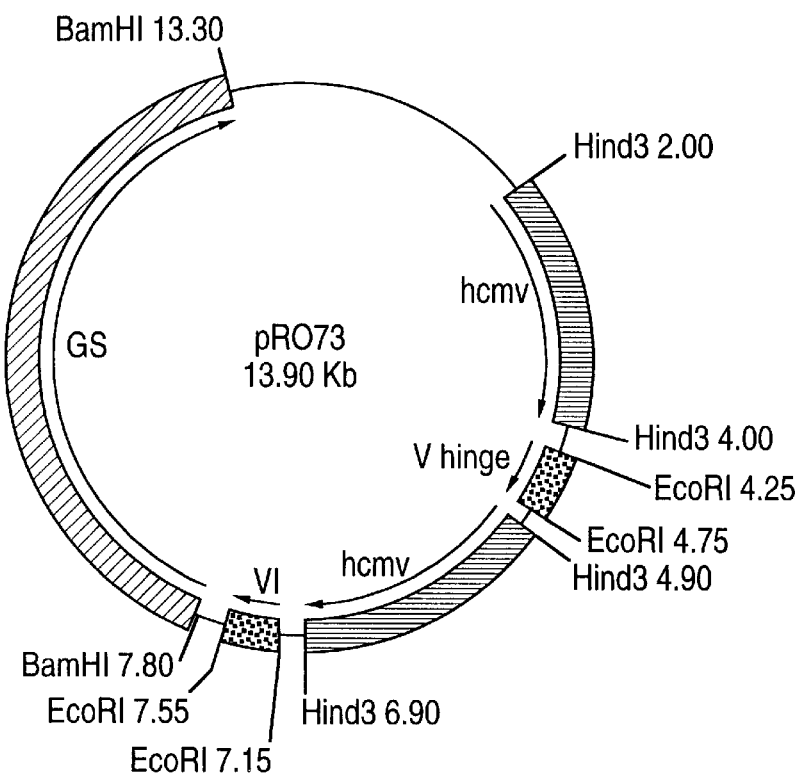
FIGS. 2A and FIG. 2B show plasmid diagrams for vectors pRO73 and pRO78.

An exemplary bivalent antigen-binding protein of the present invention was made as described below.

Vector Construction

Construction and expression of the Fv fragment of the tumour-binding antibody B72.3 has been described in International Patent Application WO 89/09825. The gene encoding the VH domain of B72.3 was isolated as a EcoRI/BglI fragment. Three pairs of oligonucleotides having the following sequences:

1. (SEQ ID NO:11) GGGCCAAGGCACCACTCTCACAGTCTC 2. (SEQ ID NO:12) GACCCCGGTTCCGTGGTGAGAGTGTCAGAGGAGT 3. (SEQ ID NO:13) CTCAGCTTCCACCAAGGGCGAGTCCAAATATGGTCC 4. (SEQ ID NO:14) CGAAGGTGGTTCCCGCTCAGGTTTATACCAAGGGGGT 5. (SEQ ID NO:15) CCCATGCCCATCAGCCCCATGATG 6. (SEQ ID NO:16) ACGGGTAGTCGGGGTACTACTTAA were ligated together to produce a BglI/EcoRI gene segment encoding a connecting structure having the sequence:(SEQ ID NO:17)

A S T K G E S K Y G P P C P S A P

Oligonucleotides numbers 1, 3 and 5 encode the sense strand and oligonucleotides 2, 4 and 6 encode the antisense strand.

The VH-encoding and connecting structure-encoding fragments were ligated together into the unique EcoRI site in expression vector pEE6.hCMV [2], to give the vector pRO71. This vector contains a gene having the nucleotide sequence and encoding the amino acid sequence shown in FIG. 1. (SEQ ID NOS:1 and 2) The encoded amino acid sequence comprise a leader sequence (amino acid residues 1 to 19), the B72.3 VH domain (amino acid residues 20 to 114) and a connecting structure (amino acid residues 115 to 132). The connecting structure comprises a joining sequence derived from a human IgG1 domain linked to a complete human IgG4 hinge region.

This gene is referred to hereafter as the VHinge gene and the polypeptide encoded thereby as the VHinge polypeptide.

Figure 2B:
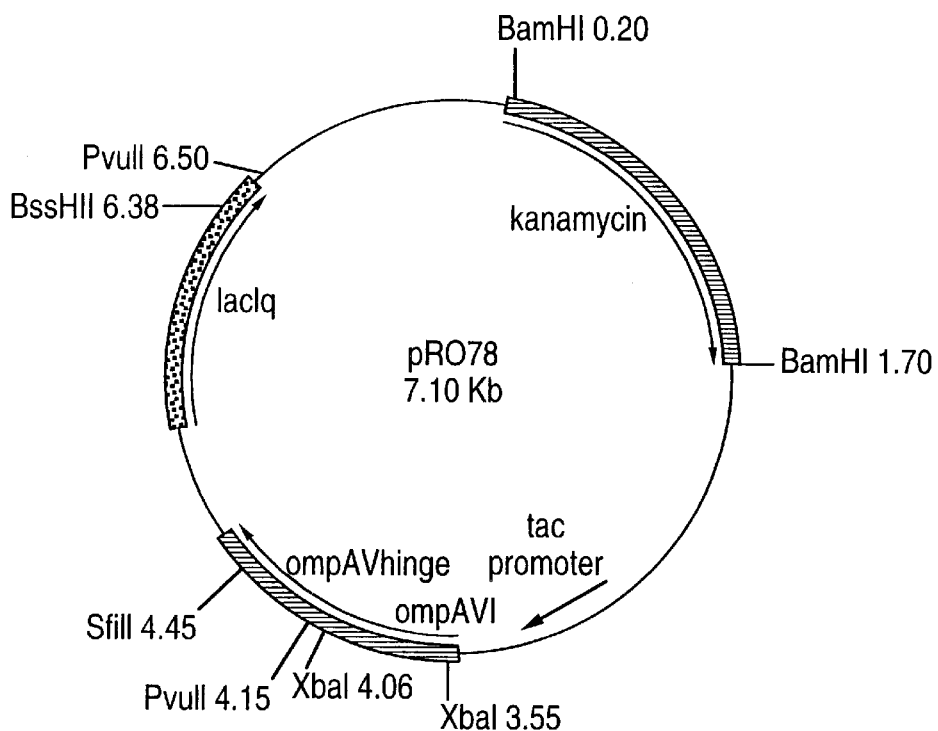

A gene encoding the VL domain of B72.3 together with a second hCMV promoter was obtained as a BglII-BamHI fragment from vector pRO18. pRO18 was produced by cloning the gene encoding the B72.3 VL domain, described in WO 89/09825, into the expression vector pEE6hCMV [2] which had been modified by changing the HindIII site at the 5' end of the hCMV promoter to a BglII site. This BglII-BamHI fragment was introduced, together with the second hCMV promoter, into the unique BamHI site of vector pRO71 to give vector pRO72. A selectable marker (glutamine synthetase) was added to vector pRO72 to produce vector pRO73. This last vector is shown diagrammatically in FIG. 2.

Another vector, labelled pRO45, was produced. This vector corresponds to vector pRO73 except that in place of the VHinge gene there is a gene encoding only the VH domain of B72.3.

Transient Expression in CHO cells

Vectors pRO45 and pRO73 were tested by transient expression in CHO cells. Synthesis and secretion of VHinge polypeptide in association with VL polypeptide from vector pRO73 and of VH polypeptide and VL polypeptide from vector pRO45 were assayed by biosynthetically labelling the expression products with $^{35}$S-methionine (100 $\mu$Ci/$10^6$ cells/ml for 48 hours). The cell supernatants were subjected to immunoprecipitation with an antiserum directed against the B72.3 VH and VL domains.

Both VHinge and VL fragments were detected in the CHO cell supernatants as 16 kD and 12 kD polypeptides respectively on reducing SDS-PAGE. The increased size of the VHinge polypeptide compared with the unmodified VH control (14 kD) was consistent with the extra length provided by the seventeen residues of the connecting structure on the C-terminal end of the VH domain.

These results indicate that the FV construct including the VHinge polypeptide was expressed intact by the CHO cells.

Expression in E. coli Cells

It has been shown that recombinant Fv fragments can be synthesised and secreted in relatively large amounts in E. coli cells [1]. Therefore, the part of the VHinge gene encoding the natural B72.3 signal sequence (residues 1 to 19) was removed and replaced with that from the prokaryotic protein ompA.

The ompA signal sequence was assembled from oligonucleotides and introduced into the cloning vector pSK (Stratagene, La Jolla, Calif., USA) to give plasmid pSKompA. The gene encoding the B72.3 VH domain without the leader sequence was obtained from pRO37 and fused to the ompA leader using oligonucleotide adapters to give plasmid pSKompAB72.3VH. In a similar way, the B72.3 VL domain was fused to the ompA leader to give the plasmid pSKompAB72.3VL.

The B72.3 VHinge sequence without the signal sequence was obtained from pRO71 as an EcoRV-EcoRI fragment and used to replace the equivalent B72.3 VH sequence in pSKompAB72.3VH to produce vector pRO76.

The ompAVHinge fragment was then isolated from pRO76 and blunt-end cloned into the unique EcoRI site of the expression vector pTQ9KanB72.3VL. This produced vector pRO78, which is shown diagrammatically in FIG. 2.

Plasmid pTQ9KanB72.3VL was constructed by introducing the B72.3 ompAVL gene from pSKompAVL into the vector pTQ9 [3] into which a kanamycin resistance gene had been introduced.

In vector pRO78, expression of the VHinge and VL genes is inducible by the addition of IPTG. Therefore, E. coli XL1 blue cells were grown to a cell density which gave $A_{600}$ of about 0.5. To this cell culture was added IPTG to 1 mM to induce expression.

The polypeptides expressed from vector pRO78were purified from the supernatants from the bacterial cells as follows. Mucin-Sepharose was prepared by coupling bovine submaxillary mucin to cyanogen bromide-activated Sepharose. The mucin-Sepharose was then packed into a column, prewashed with 0.1M citric acid and 2M KSCN and equilibrated with PBS.

Culture supernatant from the induced cells was concentrated ten fold by ultrafiltration and applied to the mucin-Sepharose column. After washing with PBS, the expressed polypeptides were eluted from the column with 0.1M citric acid, pH2. The eluted material was dialysed into PBS. The purified material was then desalted by passing it through a P10 (Sephadex G-25) column which had been equilibrated with a 0.1M acetate/citrate, 2 mM EDTA, pH 6.0 buffer and which had been preblocked with bovine serum albumin. It was shown by SDS-PAGE analysis (FIG. 3) that the purified material contained both VHinge and VL polypeptides. The identity of the polypeptides as VHinge and VL was confirmed by amino terminal sequencing.

A thiol titration experiment showed that the cysteine residue in the hinge region in the VHinge polypeptide was oxidised. Therefore, the VHinge polypeptide was partially reduced with 4.5 mM β-mercaptoethylamine for 30 minutes at 37° C. to regenerate a free thiol group in the hinge region. Oxidation, which enables the formation of a bivalent antigen-binding protein, was achieved by adding dithiopyridine to 2.2 times molar excess and incubating overnight.

Analysis of the final reaction mixture by SDS-PAGE, under both reducing and non-reducing conditions, showed that the VHinge and VL polypeptides had been associated to form dimers and the dimers had been assembled to form the desired bivalent antigen-binding protein.

It was shown that the associated VHinge-VL polypeptides could be irreversibly cross-linked into bivalent antigen-binding proteins by incubating the partially reduced product with the cross-linking reagent 1,6-bismaleimidohexane.

Figure 3:
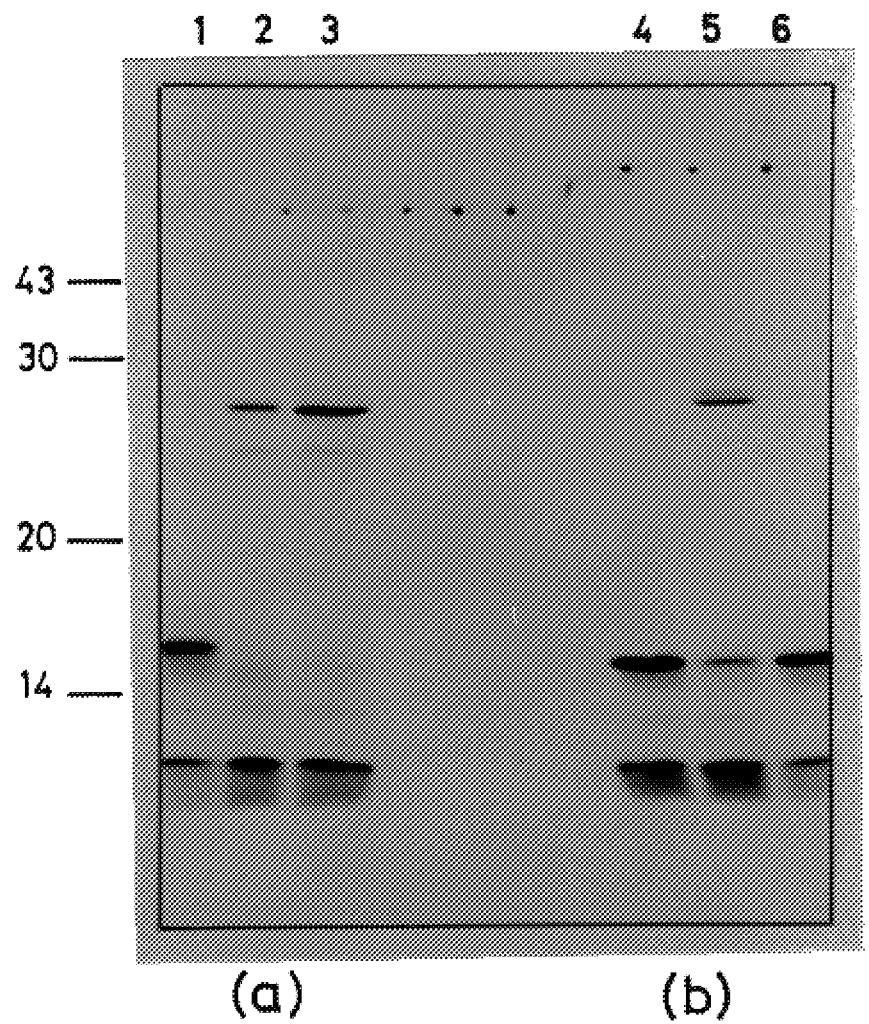
FIG. 3 shows a photograph of an SDS-PAGE gel giving an analysis of expressed polypeptides.

These results are shown in FIG. 3. In FIG. 3, panel (a) shows experiments carried out under non-reducing conditions and panel (b) shows experiments carried out under reducing conditions. The unmarked track shows molecular weight markers whose weights in kD are shown to the left of the marks. Tracks 1 and 4 represent the Fv fragment of the marks. Tracks 1 and 4 represent the Fv fragment of the B72.3 antibody. Tracks 2 and 5 represent the chemically cross-linked bivalent antigen-binding protein. Tracks 3 and 6 represent the disulphide linked bivalent antigen-binding protein.

EXAMPLE 2

Production and Analysis of Single Chain Fv (scFv) Dimeric Proteins

Figure 4:
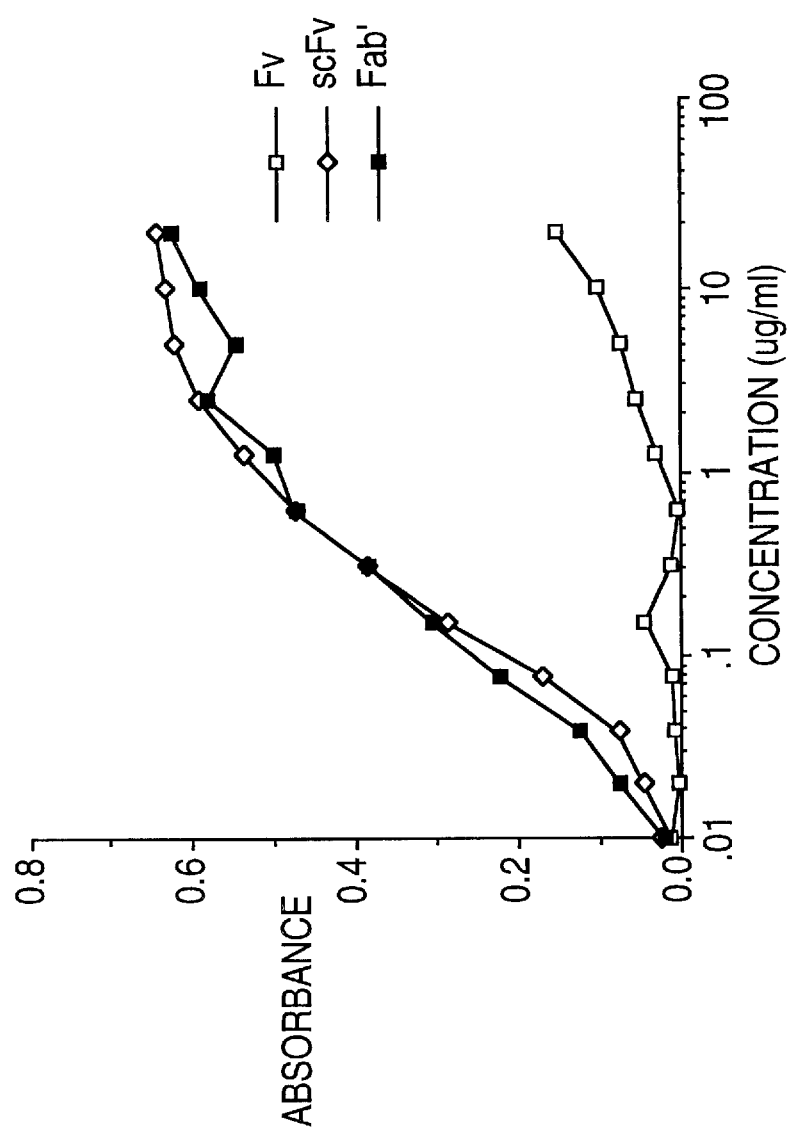
FIG. 4 shows a graph of ELISA binding assay results comparing binding of B72.3 by Fv, single chain Fv and Fab products.

In addition to the two chain heterodimer products used for preparation of bivalent Fv products, as in the previous example, single chain Fv (scFv) products have also been used for preparation of di- and multivalent products. This followed a comparative experiment (details of which are not given herein) in which monomeric B72.3 two chain heterodimer Fv, scFv and Fab products were prepared in E. coli substantially as described in Example 1. The binding activities of these three products for B72.3 antigen were compared by ELISA assay. The results obtained are given in FIG. 4 showing that the scFv and Fab products had comparable binding activities, in all cases significantly better than two chain heterodimer Fv. In particular the binding activity of the two chain heterodimer product falls off markedly at low concentration, possibly as the result of heterodimer dissociation. For this reason further experiments were carried on scFv products.

1. Construction and Expression of scFvhinge

Construction of Gene for Single Chain Fv

A gene encoding a single chain FV for B72.3 with the structure ompA-VL-15 amino acid linker VH was assembled as follows. Plasmid pSKompAB72.3 VL was doubly digested with HindIII and EcoRI and the largest fragment was gel purified. Plasmid pSKompAB72.3VH was doubly digested with PvuII and EcoRI and the approx. 320 bp fragment encoding all but the N-terminal 3 amino acids of the VH domain was gel purified. Two oligonucleotides were synthesised with the sequences shown below:(SEQ ID NOS:18 and 19)

5' AGCTTGAAATAAAACGTGGTGGCGGGGGATCCGGCGGGGGAGGTTCAGGG

3' ACTTTATTTTGCACCACCGCCCCCTAGGCCGCCCCCTCCAAGTCCC

GGTGGCGGATCCCAGGTTCAG 3'

CCACCGCCTAGGGTCCAAGTC 5'

These oligonucleotides were designed to reconstruct the C-terminal end of VL and the N-terminal of VH joined together by a 15 amino acid peptide linker of sequence (gly gly gly gly ser)×3. (Amino acid residues 8–220 (SEQ ID NO:21). These oligonucleotides were annealed and ligated with the two purified fragments. The ligation mixture was transformed into competent cells of the E. coli strain XL1 Blue and clones identified by DNA sequencing which possessed the correct sequence from a position 5' to the HindIII site of VL through to a position 3' to the PvuII site of VH, as shown below: and in SEQ ID NOS:20 and 21

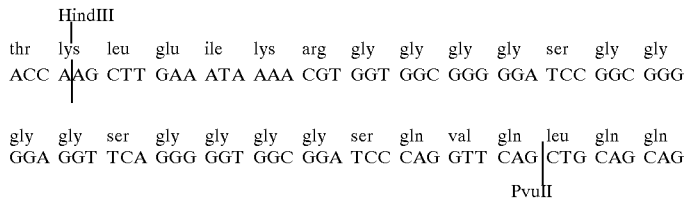

The XhoI-EcoRI fragment carrying the ompA-VL-linker-VH sequences was subcloned from one of these clones into the expression vector pTQ9kan doubly digested with SalI and EcoRI. The resulting plasmid was designated pQ9KSCFv3.

Construction and Expression of Single Chain Fv-hinge Plasmids

Plasmid pQ9KSCFv3 was doubly digested with SfiI and BssHII and the smaller fragment replaced with the equivalent fragment from pRO77 to generate plasmid pRO93, which therefore carries a single chain Fv variant with the 17 amino acid hinge sequence on the C-terminal end of VH domain. This single chain Fvhinge polypeptide was expressed in E. coli strain X11 Blue and recovered from supernatants of IPTG induced cultures as described for the native Fvhinge fragments.

To investigate the length of the hinge/linker sequence required to produce bivalent single chain molecules, a second shortened hinge version single chain Fv-hinge construct was made. In this construct, the human IgG4 (Cys to Ala) sequence was fused directly to the C-terminus of B72.3 VH without the 5 amino acid spacer element derived from the N-terminus of human CH1 heavy chain IgG CH1 domain. The sequence of this construct is shown in FIG. 5. (SEQ ID NOS:3 and 4)

The modified single chain Fv-hinge was constructed using the polymerase chain reaction as described below [ref. 4]. Using the plasmid, pSKompAB72.3 VH, as a template, a fragment was generated by PCR with the following flanking oligonucleotide primers:

VH or VL domains. In this way the following variants were produced (SEQ ID NOS:24–26) (amino acid changes are underlined):

A S T K G E S T̲ Y G P P C P S A P A S T T̲ G E S K
Y G P P C P S A P A S T T̲ G E S T̲ Y G P P C P S A P

These sequences were fused to the C-terminus of B72.3 VH cloned into the pTQ vector and shown to be expressed in E. coli.

2. Purification of scFvhinge

B72.3 scFvhinge products were purified from E. coli culture supernatant using affinity chromatography on mucin-sepharose. Bovine sub-maxillary mucin was coupled to CNBr-activated Sepharose 4B at 30 mg/ml Sepharose by standard techniques. The column was pre-washed with 2M potassium thiocyanate and 0.1M citric acid and equilibrated in PBS. The E. coli supernatant was clarified by centrifugation and filtration and the pH adjusted to greater than 7. A cocktail of protease inhibitors was added to the culture supernatant to protect against proteolytic degradation of the scFvhinge. The cocktail consisted of EDTA (1 mM), aprotinin (5 μg/ml), leupeptin (1 μg/ml), pepstatin A (1 μg/ml), benzamidine (1 mM), antipain (1 μg/ml) and phenylmethylsulphonyl flouride (1 mM). The sample was loaded onto the column which was then washed with PBS and eluted with 0.1M citric acid pH2. The column was washed before re-use with 2M potassium thiocyanate. The purified scFvhinge was pH adjusted to 7 immediately on elution from the column and concentrated by ultrafiltration.

The purification of scFvhinge products on mucin-sepharose is efficient in that under these conditions the Forward primer: (SEQ ID NO:22) 5'  CCCCCCCTCGAGTTCTAGATAACGA 3'

Reverse primer: (SEQ ID NO:23) 5'  GCGCGAATTCATCATGGGGCTTGATGGGCATGGGGGA
CCATATTTGGACTCTGAGGAGACTGTGAGAGTGGTGCC
TTG 3'

The resulting fragment was restricted with XhoI and EcoRI and cloned into the vector pSK to give the plasmid pRO94. A XhoI-EcoRI fragment was recovered from this plasmid and cloned into the pTq9 vector to produce plasmid pRO96. The new B72.3 VHinge sequence was incorporated into the single chain Fv vector through SfiI/BssHII restriction sites to generate the plasmid pRO97.

The pRO97 plasmid was expressed in E. coli XL1 Blue and the single chain Fv-hinge polypeptide purified from the cell supernatants of IPTG induced cultures as described for the native Fv-hinge fragments.

The same approach can be used to produce other hinge/linker sequences that could be attached to the C-terminus of scFvhinge is bound and eluted quantitatively. The purity of scFvhinge purified in this manner is typically>95%, with the majority of the purified protein in the form of monomer.

3. Formation of Dimeric scFvhinge

Purified scFvhinge was buffer exchanged into phosphate buffered saline pH7 containing 2 mM EDTA and partially reduced by the addition of dithiothreitol to 20 mM followed by incubation at room temperature for one hour. This procedure routinely generates a free thiol in the hinge region without disrupting the internal disulphide bonds of the folded VH and VL domains. The number of free thiols was checked by titration with 4,4'-dithiodipyridine using a standard spectrophotometric assay [ref. 5] and the reduced scFvhinge used to form the dimeric species. Disulphide linked dimer was produced by incubating reduced scFvhinge in a 2.2 fold molar excess over 4,4'-dithiodipyridine at room temperature overnight. The dimeric material was then purified away from the unreacted monomer by HPLC gel filtration on a DuPont Zorbax GF-250 column run in 0.2M phosphate buffer pH7.0. Chemically cross-linked dimer was produced by reacting the reduced scFvhinge in a 2.2 fold molar excess over 1,6-bismaleimidohexane at room temperature overnight. The cross-linked dimer was again purified away from residual scFvhinge by gel filtration HPLC.

4. Analysis of Dimer scFvhinge

Figure 6:
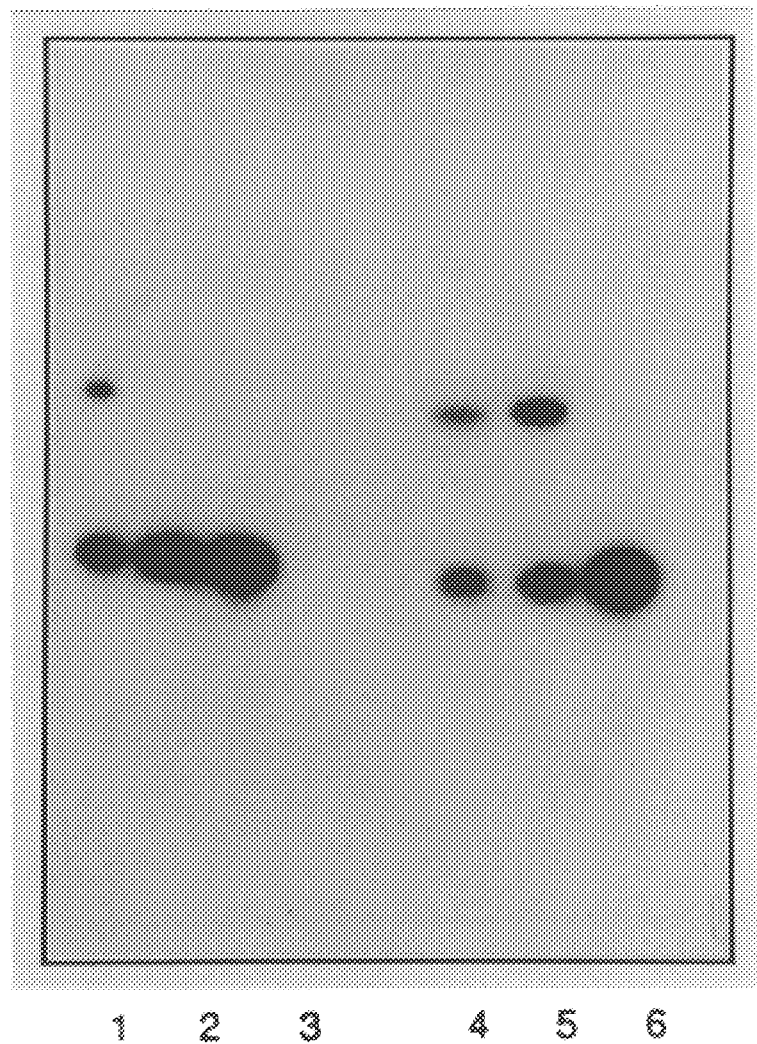
FIG. 6 shows an autoradiograph of an SDS-PAGE gel of scFvhinge, disulphide linked dimer and cross-linked dimer under both reduced and non-reduced conditions.
Figure 7:
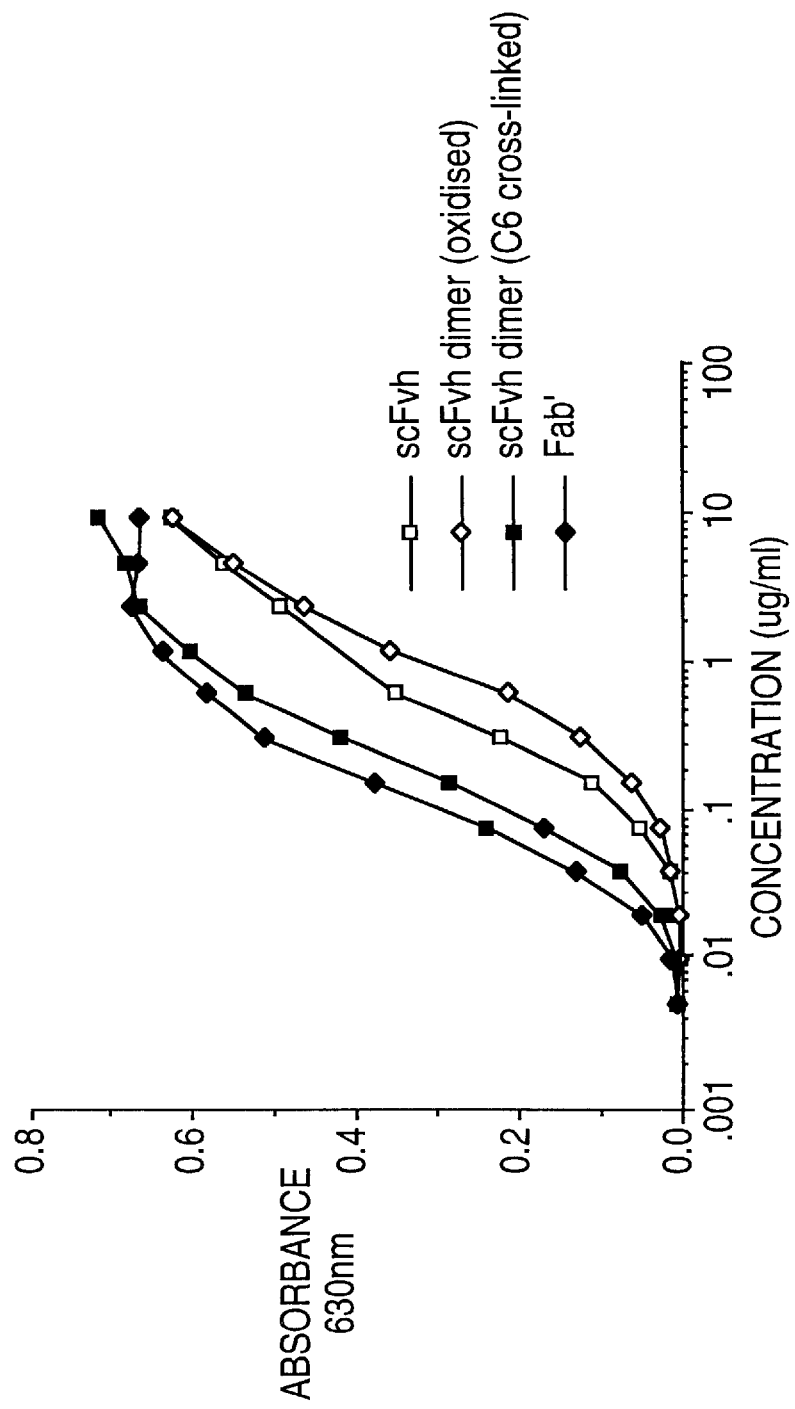
FIG. 7 shows a graph of ELISA binding assay results comparing binding of B72.3 by monomeric scFvhinge, oxidised scFvhinge dimer and chemically cross-linked scFvhinge dimer.

SDS-PAGE analysis of the diners revealed the expected molecular weight for the dimers of approximately 56 kDa and this was maintained on labelling with $^{125}$I (see FIG. 6). Antigen binding assays using an ELISA format revealed a significant improvement in the ability of the dimeric species (disulphide and chemically cross-linked) to bind to the antigen compared to scFvhinge which had itself been shown to possess full antigen binding activity compared to Fab' standard (FIG. 7).

Figure 8:
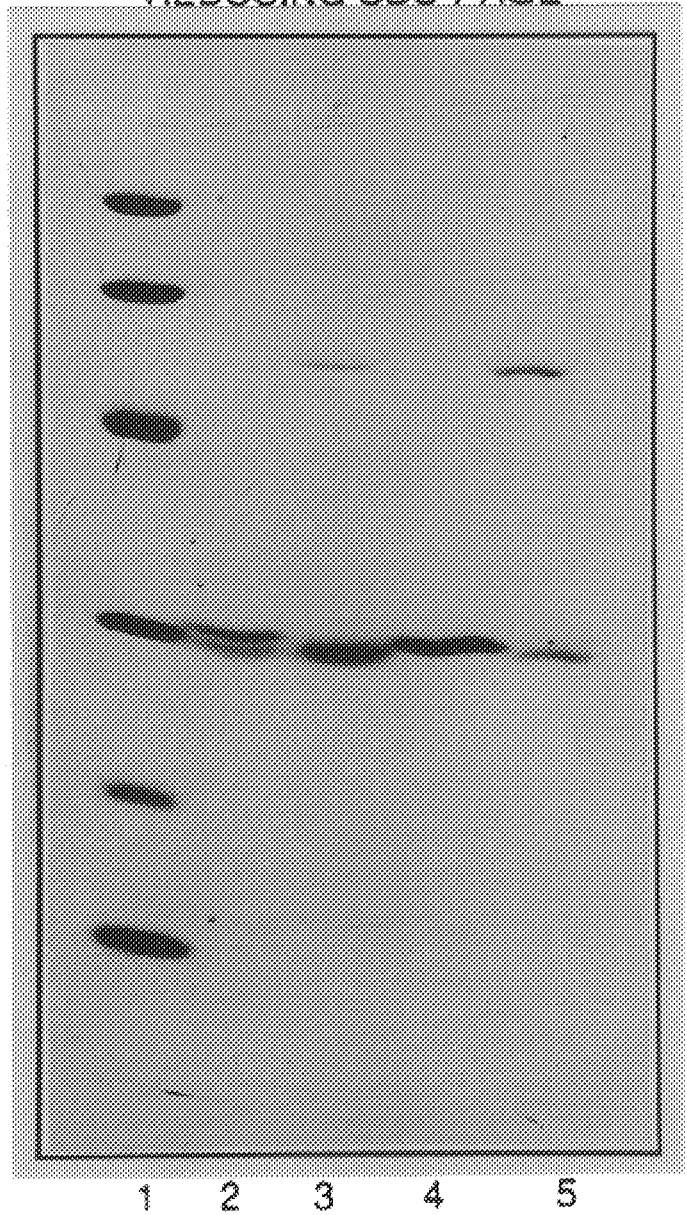
FIG. 8 shows SDS-PAGE gel results comparing both monomeric and dimer cross-linking mix, for the full length scFvhinge product and the shortened hinge version of scFvhinge from plasmid pRO97.
Figure 9:
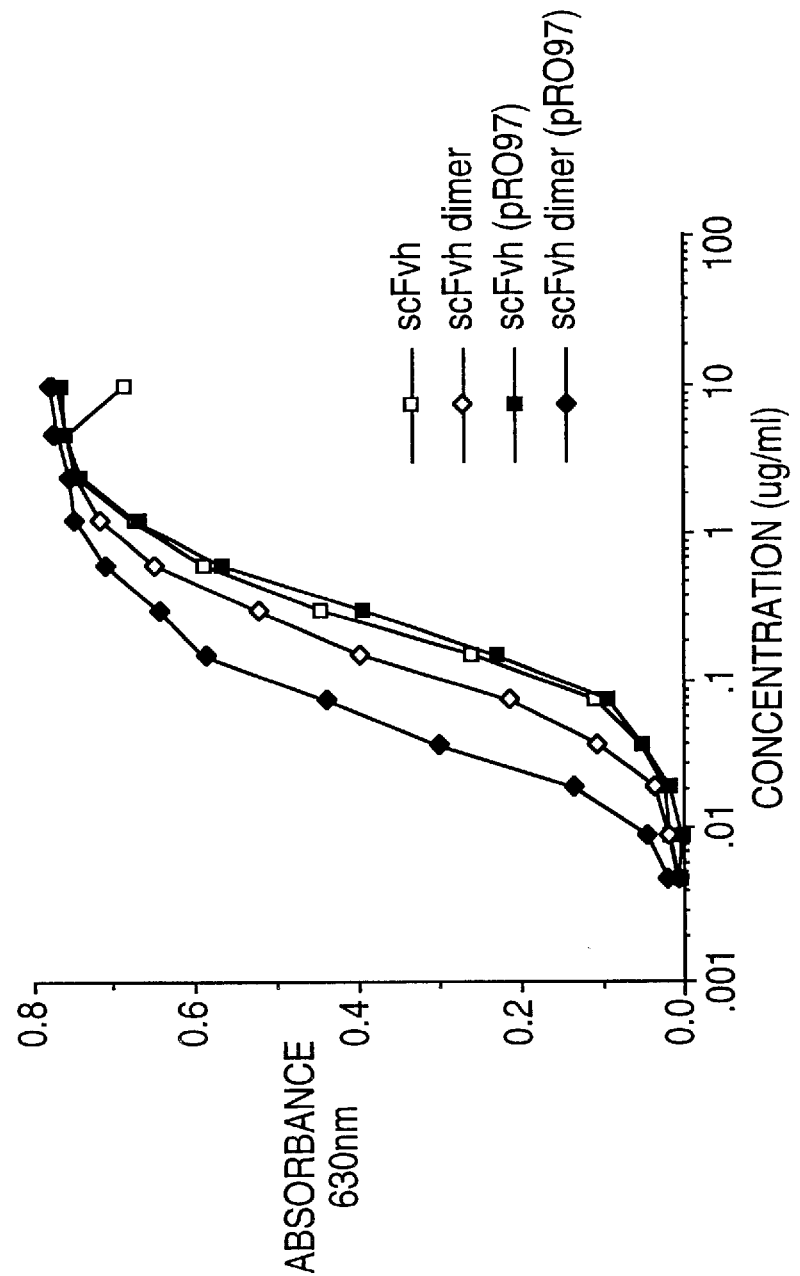
FIG. 9 shows a graph of ELISA binding assay for the proteins shown in FIG. 8.

Similarly, the shortened hinge version of scFvhinge produced by pRO97 was purified and dimeric species prepared and tested as described above for the full length scFvhinge product. The results obtained are given in FIG. 8 (showing reducing SDS-PAGE results for scFvhinge monomer and dimer cross-linking mix for both the full length and shortened hinge versions) and FIG. 9 (ELISA binding assay results for the same products.

The ability of the full length scFvhinge dimers to target tumours in vivo was tested in a mouse xenograft experiment. ScFvhinge and the dimeric species (disulphide and chemically cross-linked) were labelled with $^{125}$I to a specific activity of approximately 0.1 µCi/µg using Bolton Hunter reagent by standard methodology. Labelling by this method resulted in the retention of immunoreactivity. Groups of 4 nude mice bearing subcutaneous LS174T tumours on the flanks were injected with approximately 7 µg of scFvhinge monomer or dimeric species (disulphide and chemically cross-linked) as appropriate and groups of animals killed at specific times to determine biodistributions. The biodistribution was determined by collecting samples of blood, muscle, femur, lung, liver, spleen, kidney, colon and tumour which were weighed dissolved in 7M potassium hydroxide and counted in an LKB model 1270 gamma counter. Results were expressed as the mean percentage of the injected dose per gram of tissue±the standard deviation.

Figure 10:
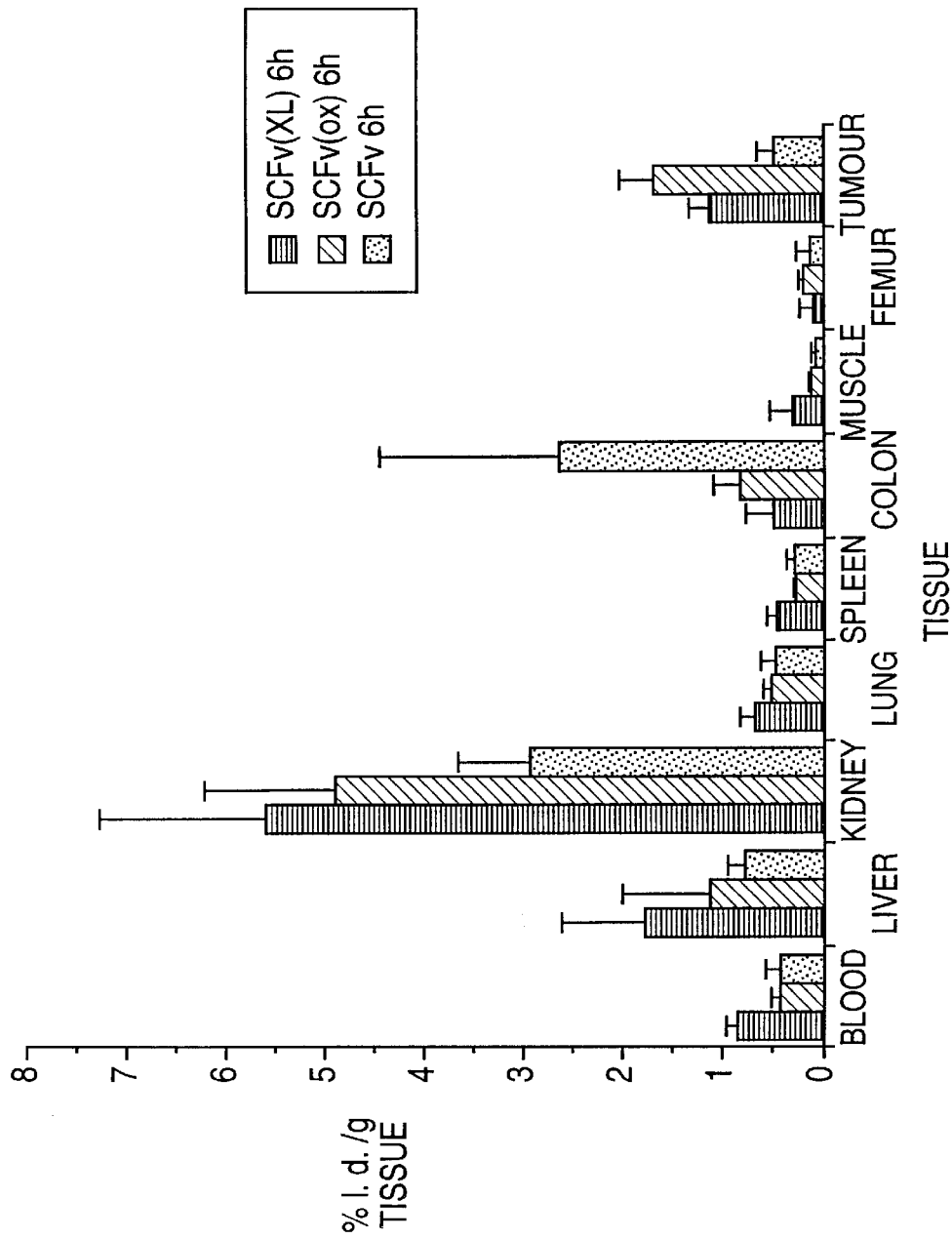
FIG. 10 shows a histogram giving results of biodistribution studies on the proteins shown in FIG. 8.

Results of the biodistribution analysis revealed that the scFv dimeric species bound to the tumour more effectively than the scFvhinge monomer and resulted in higher tumour-:blood ratios (FIG. 10).

Formation and Analysis of Trimeric scFvhinge

Full length ScFvhinge produced as described above and reduced under the same conditions as above was cross-linked to trimer by incubation with tri-maleimide linker (CT557). The preparation of CT557 is described in our copending British patent application, entitled "Chemical Compounds" of even date herewith. Reduced scFvhinge in PBS/EDTA pH7.0 was incubated with CT557 at a molar ratio of 6.6:1, scFvhinge:CT557 for overnight at room temperature. This procedure resulted in the formation of trimer as judged by SDS-PAGE analysis which was purified using mixed mode ion-exchange on Bakerbond Abx. The trimer crude mix was dialysed in 0.1M sodium acetate pH5.5 and applied to an Abx column equilibrated with the same buffer. After washing with the same buffer the trimer was eluted with 100 mM sodium acetate pH6.7 containing 1M ammonium sulphate. The purified trimer was then dialysed into PBS for further analysis.

Figure 11:
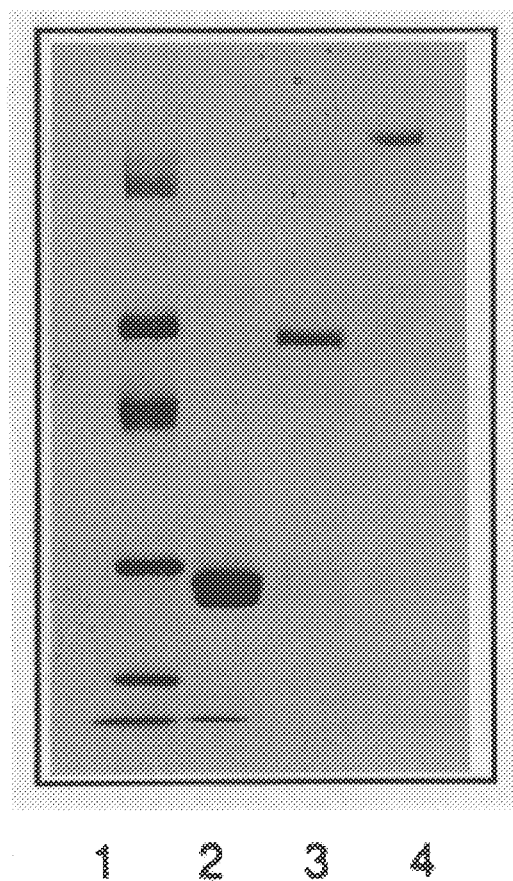
FIG. 11 shows a SDS-PAGE gel showing purified scFvhinge trimer compared to dimer and monomer.
Figure 12:
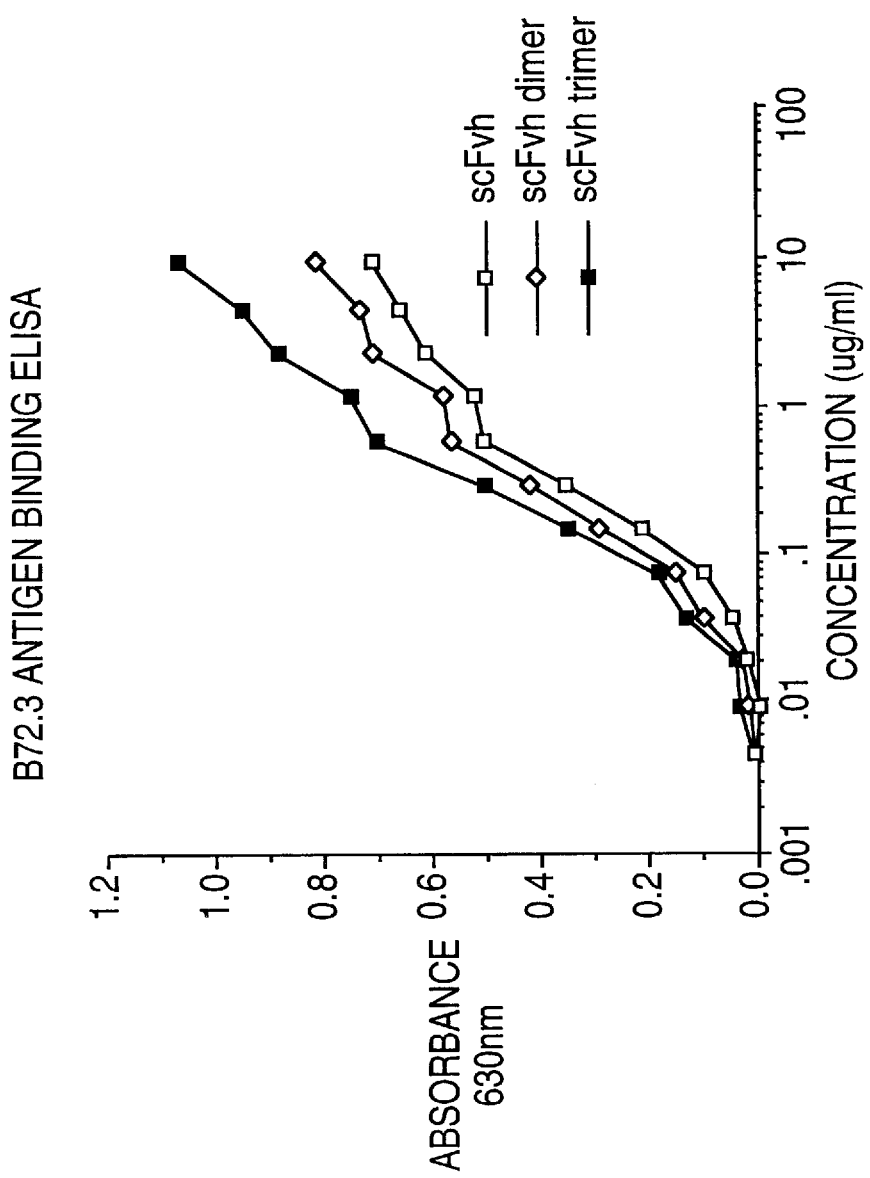
FIG. 12 shows a graph of ELISA binding assay results comparing scFvhinge monomer, dimer and trimer products.
Figure 13:
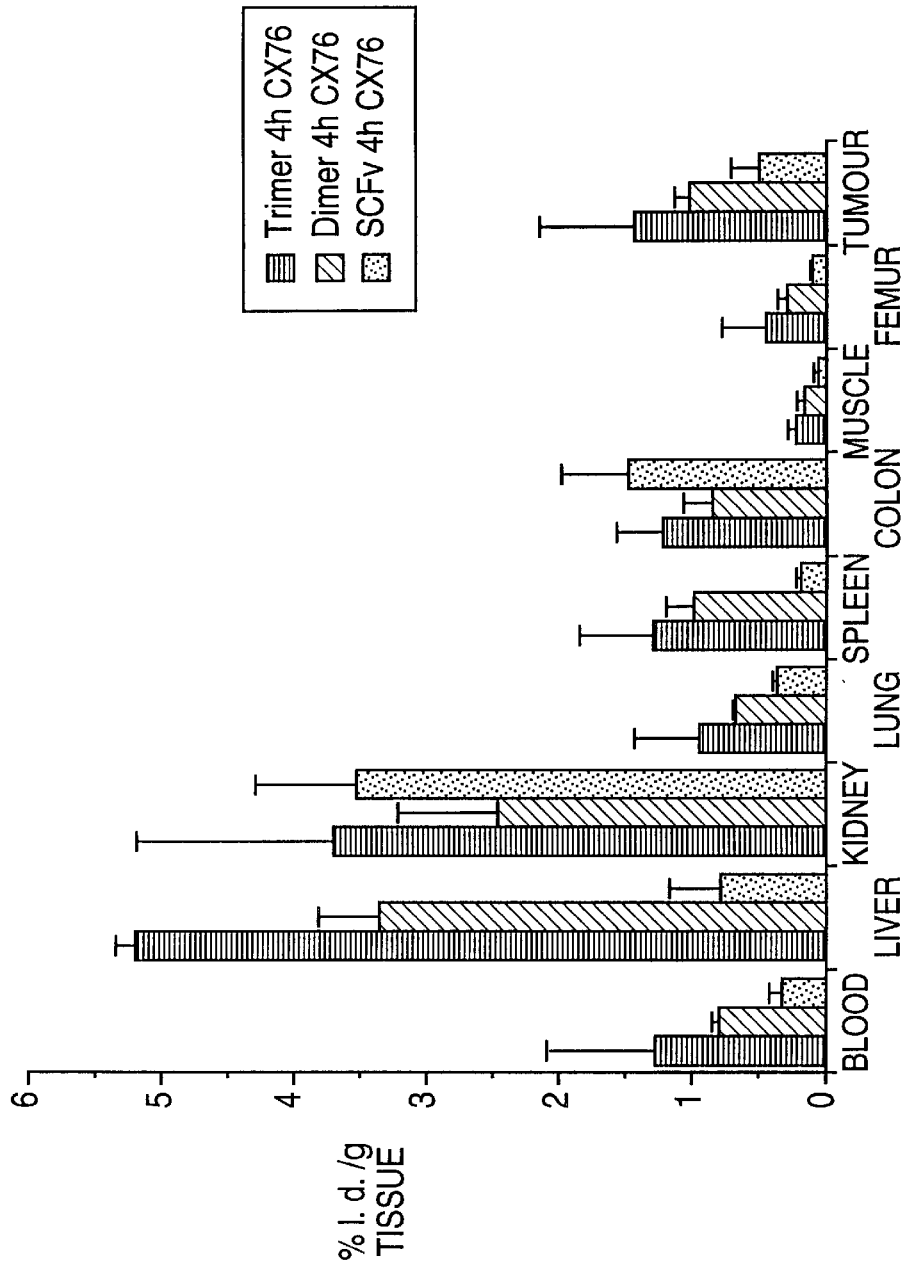
FIG. 13 shows a histogram giving results of biodistribution studies of tumour localisation of scFvhinge monomer, dimer and trimer species.

SDS-PAGE revealed a band of approximately 85 kDa (FIG. 11) corresponding to purified trimer and ELISA antigen-binding assays demonstrated that the trimer bound to the antigen more effectively than both the dimer and the monomer (FIG. 12). This increased ability to bind to the antigen was also observed in vivo. A biodistribution experiment in a mouse LS174T xenograft model revealed increased levels of scFvhinge trimer localised to the tumour compared to both the dimer and the monomer (FIG. 13).

Formation of Tetrameric scFvhinge

Figure 14:
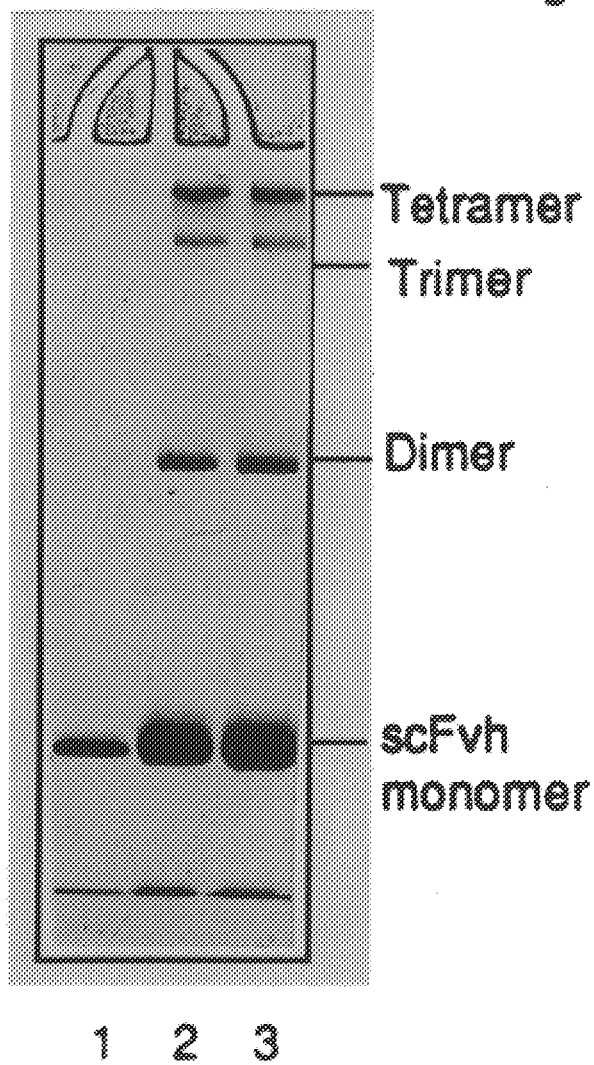
FIG. 14 shows a reducing SDS-PAGE gel showing formation of tetrameric scFvhinge.

Tetrameric scFvhinge was produced using reduced scFvhinge produced in the same way as described above. The reduced scFvhinge was then incubated with tetramaleimide linker (CT558) at a molar ratio of 8.8:1, scFvhinge:CT558 overnight at room temperature. The preparation of CT558 is described in our copending British patent application, entitled "Chemical Compounds", of even date herewith. Formation of tetrameric scFvhinge was demonstrated by SDS-PAGE analysis (FIG. 14).

It will be appreciated that the present invention has been described above by way of example only and that modifications and variations may be made by the skilled man without departing from the scope of the present invention.

LIST OF REFERENCES

[1] Skerra, A. and Pluckthun, A., Science, 240, 1038–1041, 1988.

[2] Stephens, P. E. and Cockett, M. I., Nuc. Acids. Res., 17, 7110, 1989.

[3] Stark, M. J., Gene, 51, 255–267, 1987.

[4] PCR Technology: Principles and Applications for DNA Amplification (ed. H. A. Erlich), Macmillan 1989.

[5] Lyons, A., King, D. J., Owens, R. J., Yarranton, G. T., Millican, A., Whittle, N. R., and Adair, J. R., (1990), Protein Engineering, 3, 703–708.

What is claimed is:

1. An antigen-binding protein, comprising:
    (a) 3 or 4 $V_H$ domains;
    (b) a spacing polypeptide attached to the C-terminal end of each $V_H$ domain;
    (c) a linkage polypeptide, containing linkable residues, attached to the C-terminal end of each spacing polypeptide;
    (d) a $V_L$ domain associated with each $V_H$ domain to form antigen-binding $F_v$ fragments,
    wherein said linkage polypeptides are cross-linked via their linkable residues and wherein the $F_v$ fragments are spaced so that each can bind an antigenic determinant.

2. A protein according to claim 1, wherein each linkage polypeptide comprises the core section of an antibody hinge and wherein the cross-linkage is via disulfide bonds.

3. A protein according to claim 1, wherein said linkable residues are selected from the group consisting of cysteine, lysine, glutamic acid and aspartic acid.

4. A protein according to claim 1, wherein each spacing polypeptide attached to each maleimide moiety is selected from the group consisting of a $V_H$—$C_H1$ polypeptide chain and a $V_L$—$C_L$ polypeptide chain.

5. A protein according to claim 4, wherein the spacing polypeptide further comprises the N-terminal part of an antibody hinge region.

6. A protein according to claim 1, wherein the spacing polypeptide is selected from the group consisting of the following amino acid sequences:
    (a) A S T K G E S K Y (amino acid residues 1–10 of SEQ ID NO:5),
    (b) A S T K G E R K (amino acid residues 1–8 of SEQ ID NO:6), and
    (c) A S T K G E L K T (amino acid residues 1–9 of SEQ ID NO:7).

7. A protein according to claim 1, wherein the linkage polypeptide is selected from the group consisting of the following amino acid sequences:
    (a) P P C P S A P (amino acid residues 11–17 of SEQ ID NO:5),
    (b) C C V E C P P C P (amino acid residues 9–17 of SEQ ID NO:6), and
    (c) P L G T T H T C P R C P (E P K S C D T P P P C R C P)$_n$, (when n=0, amino acid residues 10–21 of SEQ ID NO:7; when n=1, amino acid residues 10–35 of SEQ ID NO:8; when n=2, amino acid residues 10–49 of SEQ ID NO:9; when n=3, amino acid residues 10–63 of SEQ ID NO:10).

8. A protein according to claim 1, wherein said protein has only one antigen-specificity.

9. A protein according to claims 1, wherein said protein has multiple antigen-specificities.

10. A protein according to claim 1, wherein one or more of the $F_v$ fragments is a single chain $F_v$.

11. An antigen binding protein, comprising:
    (a) a linkage unit comprising a maleimide moiety selected from the group consisting of trimaleimides and tetramaleimides;
    (b) a spacing polypeptide attached to each maleimide moiety in said linkage unit by the C-terminus of the spacing polypeptide; and
    (c) 3 to 4 $V_H$ domains each attached by its C-terminus to each spacing polypeptide, via a peptide bond,
    wherein each $V_H$ domain is associated with a $V_L$ domain to form an antigen-binding $F_v$ fragment, and in which the $F_v$ fragments are spaced so that each can bind an antigenic determinant.

12. A protein according to claim 11, wherein each spacing polypeptide attached to each maleimide moiety is 3 to 16 amino acid residues long.

13. A protein according to claim 12, wherein each spacing polypeptide attached to each maleimide moiety is 7 to 12 amino acid residues long.

14. A protein according to claim 13, wherein each spacing polypptide attached to each maleimide moiety is 10 amino acid residues in length.

15. A protein according to claim 11, wherein each spacing polypeptide is selected from the group consisting of a $V_H$—$C_H1$ polypeptide chain and a $V_L$—$C_L$ polypeptide chain.

16. A protein according to claim 11, wherein said protein has only one antigen-specificity.

17. A protein according to claim 11, wherein said protein has multiple antigen-specificities.

18. A protein according to claim 11, wherein one or more of the $F_v$ fragments is a single chain $F_v$.

19. A monospecific antigen binding protein comprising:
(a) a linkage unit comprising a malemide moiety selected from the group consisting of trimaleimides and tetramaleimides;
(b) a spacing polypeptide attached to each maleimide moiety in said linkage unit; and
(c) 3 to 4 $V_H$ domains each attached by its C-terminus to each spacing polypeptide, via a peptide bond,
wherein each $V_H$ domain is associated with a $V_L$ domain to form an antigen-binding $F_v$ fragment, and in which the $F_v$ fragments are spaced so that each can bind an antigenic determinant.

20. A monospecific antigen-binding protein comprising:
(a) 3 or 4 VH domains;
(b) a spacing polypeptide attached to the C-terminal end of each $V_H$ domain;
(c) a linkage polypeptide, containing linkable residues attached to the C-terminal end of each spacing polypeptide;
(d) a $V_L$ domain associated with each $V_H$ domain to form antigen-binding $F_v$ fragments,
wherein said linkage polypeptides are cross-linked via their linkable residues and wherein the $F_v$ fragments are spaced so that each can bind an antigenic determinant.

21. An antigen-binding protein, comprising:
(a) 3 to 4 $V_H$ domains;
(b) a spacing polypeptide attached to the C-terminal end of each $V_H$ domain;
(c) a linkage polypeptide, containing linkable residues, attached to the C-terminal end of each spacing polypeptide;
(d) a $V_L$ domain associated with each $V_H$ domain to form antigen-binding $F_v$ fragments,
wherein each linkage polypeptide is cross-linked via their linkable residues and wherein the $F_v$ fragments are spaced so that each can bind an antigenic determinant.

* * * * *